United States Patent
Dhawan

(10) Patent No.: US 9,572,494 B2
(45) Date of Patent: Feb. 21, 2017

(54) METHOD AND APPARATUS FOR MULTI-SPECTRAL IMAGING AND ANALYSIS OF SKIN LESIONS AND BIOLOGICAL TISSUES

(75) Inventor: Atam Prakash Dhawan, Randolph, NJ (US)

(73) Assignee: New Jersy Institute of Technology, Newark, NJ (US)

( * ) Notice: Subject to any disclaimer, the term of this patent is extended or adjusted under 35 U.S.C. 154(b) by 572 days.

(21) Appl. No.: 12/539,049

(22) Filed: Aug. 11, 2009

(65) Prior Publication Data

US 2010/0042004 A1 Feb. 18, 2010

Related U.S. Application Data

(60) Provisional application No. 61/088,170, filed on Aug. 12, 2008.

(51) Int. Cl.
*A61B 5/05* (2006.01)
*A61B 5/00* (2006.01)

(52) U.S. Cl.
CPC ............. *A61B 5/0059* (2013.01); *A61B 5/411* (2013.01); *A61B 5/443* (2013.01); *A61B 5/444* (2013.01); *A61B 5/445* (2013.01); *A61B 5/7264* (2013.01)

(58) Field of Classification Search
USPC ............... 600/301, 306, 310, 320, 323, 364, 416,600/419, 472, 473, 476; 356/3.11, 3.14, 4.01, 356/4.03, 5.14, 40, 41; 382/128

See application file for complete search history.

(56) References Cited

U.S. PATENT DOCUMENTS

| | | | |
|---|---|---|---|
| 5,435,309 A * | 7/1995 | Thomas et al. | 600/310 |
| 6,141,577 A * | 10/2000 | Rolland et al. | 600/407 |
| 6,208,749 B1 * | 3/2001 | Gutkowicz-Krusin et al. | 382/128 |
| 6,625,785 B2 * | 9/2003 | Chatterjee et al. | 716/136 |
| 2003/0064025 A1 * | 4/2003 | Yang et al. | 424/9.6 |
| 2004/0037455 A1 * | 2/2004 | Klingensmith | A61B 5/02007 382/128 |
| 2005/0030372 A1 * | 2/2005 | Jung et al. | 348/77 |
| 2006/0139640 A1 * | 6/2006 | Mullani | 356/369 |
| 2006/0276966 A1 * | 12/2006 | Cotton et al. | 702/1 |
| 2007/0058860 A1 * | 3/2007 | Harville et al. | 382/167 |
| 2007/0189298 A1 * | 8/2007 | Wong et al. | 370/395.1 |

(Continued)

OTHER PUBLICATIONS

Claridge et al., An inverse method for recovery of tissue parameters from colour images, Information Processing in Medical Imaging. Springer, Berlin, LNCS2732, pp. 306-317 (2003).

(Continued)

*Primary Examiner* — Unsu Jung
*Assistant Examiner* — Michael N Fisher
(74) *Attorney, Agent, or Firm* — Timothy X. Gibson; Gibson & Dernier LLP

(57) ABSTRACT

A multispectral nevoscope that uses specific wavelengths in the visible and infrared spectrum of electromagnetic radiation to transilluminate a skin-lesion or a biological tissue or specimen for imaging and maps multispectral 2-dimensional images into 3-dimensional virtual space for providing 3-D distributions of pre-defined parameters representing the characteristic properties (such as melanin, hemoglobin and deoxyhemoglobin, etc.) of a skin lesion. Methods are disclosed for analyzing and using the characteristic distributions of specific parameters for detection and management of skin-cancers, or characterization of a biological tissue or specimen.

17 Claims, 16 Drawing Sheets

(56) References Cited

U.S. PATENT DOCUMENTS

2007/0192241 A1* 8/2007 Metlapalli ................ 705/38

OTHER PUBLICATIONS

Ganster et al., Computer aided recognition of pigmented skin lesions, Melanoma Research, vol. 7(Supp. 1) S19-20 (1997).
Seidenari et al., Digital video-microscopy and image analysis with automatic classification for detection of thin melanomas, Melanoma Research 9(2), 163-171 (1999).
Menzies et al., Automated instrumentation and diagnosis of invasive melanoma, Melanoma Research, vol. 7 (Supp. 1), S13 (1997).
Claridge et al., From color to tissue histology: Physics-based interpretation of images of pigmented skin lesion, Medical Image Analysis vol. 7, pp. 489-502 (2003).
Tomatis et al., Automated melanoma detection: multi-spectral imaging and neural network approach for classification, Med. Phys. 30(2), pp. 212-221 (2003).
Tomatis et al., Spectrophotometric imaging of subcutaneous pigmented lesions: discriminant analysis, optical properties and histological characteristics, J. Photochem. Photobiol., B 42, 32-39 (1998).
S. Srinath Maganti, Hree-Dimensional Optical Tomographic Image Reconstruction from Nevoscope Images, Ph.D. Dissertation, Advisor: Atam P. Dhawan, University of Cincinnati (1997).
S. Maganti and A.P. Dhawan, 3-D Nevoscope image reconstruction using diverging ray ART, SPIE, vol. 3032, pp. 340-348 (1997).
W. Grohman and A.P. Dhawan, Fuzzy convex set based pattern classification of mammographic microcalcifications, Pattern Recognition, vol. 34(7), pp. 1469-1482 (2001).
Wang et al., MCML-Monte Carlo modeling of light transport in multi-layered tissues, Computer Methods and Programs in Biomedicine 47 (1), 131-146 (1995).
R. Anderson et al., The optics of human skin, Journal of Investigative Dermatology, vol. 77(1), 13-19 (1981).
A.Bashkatov et al., Optical properties of human skin, subcutaneous and mucous tissues in the wavelength range from 400 to 2000nm, Journal of Physics D: Applied Physics, vol. 38, 2543-2555 (2005).
M. van Gemert et al., Skin Optics, IEEE Transactions on Biomedical Engineering, vol. 36(12), 1146-1154 (1989).
I. Meglinski et al., Quantitative assessment of skin layers absorption and skin reflectance spectra simulation in the visible and near-infrared spectral regions, Physiol. Meas, 23, 741-753 (2002).
S. Prahl, Oregon Medical Laser Center, Optical absorption of hemoglobin, http://omlc.org/spectra/hemoglobin/index.html pp. 1-3 (1999).
D. Whitley, A Genetic Algorithm Tutorial, Technical Report CS-93-103, pp. 1-37, Colorado State University (1993).
Busetti, Genetic algorithms overview, http://www.geocities.com/francorbusetti/gaweb.pdf, pp. 1-13 (2001).
Beasley et al., An overview of genetic algorithms: Part 1, Fundamentals, University Computing, 15(2), 58-69 (1993).
Beasley et al., An Overview of Genetic Algorithms: Part 2, Research topics, University Computing, University of Cardiff, 15(4), 170-181 (1993).
Ingber et al., Genetic Algorithms and Very Fast Simulated Annealing: Comparison, Mathematical and Computer Modelling 16(11), 87-100 (1992).
Goldberg, Genetic Algorithms in Search, Optimization, and Machine Learning, Addison-Wesley Pub. Co., Chapter 3: pp. 60-87 (1989).
C. Houck et al., A Genetic Algorithm for Function Optimization: a Matlab Implementation, NCSU-IE TR 95-09, pp. 1-14 (1995).
Dzung L. Pham, et al., Adaptive Fuzzy Segmentation of Magnetic Resonance Images, IEEE Transactions on Medical Imaging, vol. 18, No. 9, pp. 737-752, (1999).
A. K. Jain and R. C. Dubes, Algorithms for Clustering Data, Prentice Hall, Chapters 3 and 4: pp. 55-222, Englewood Cliffs, NJ, (1998).

* cited by examiner

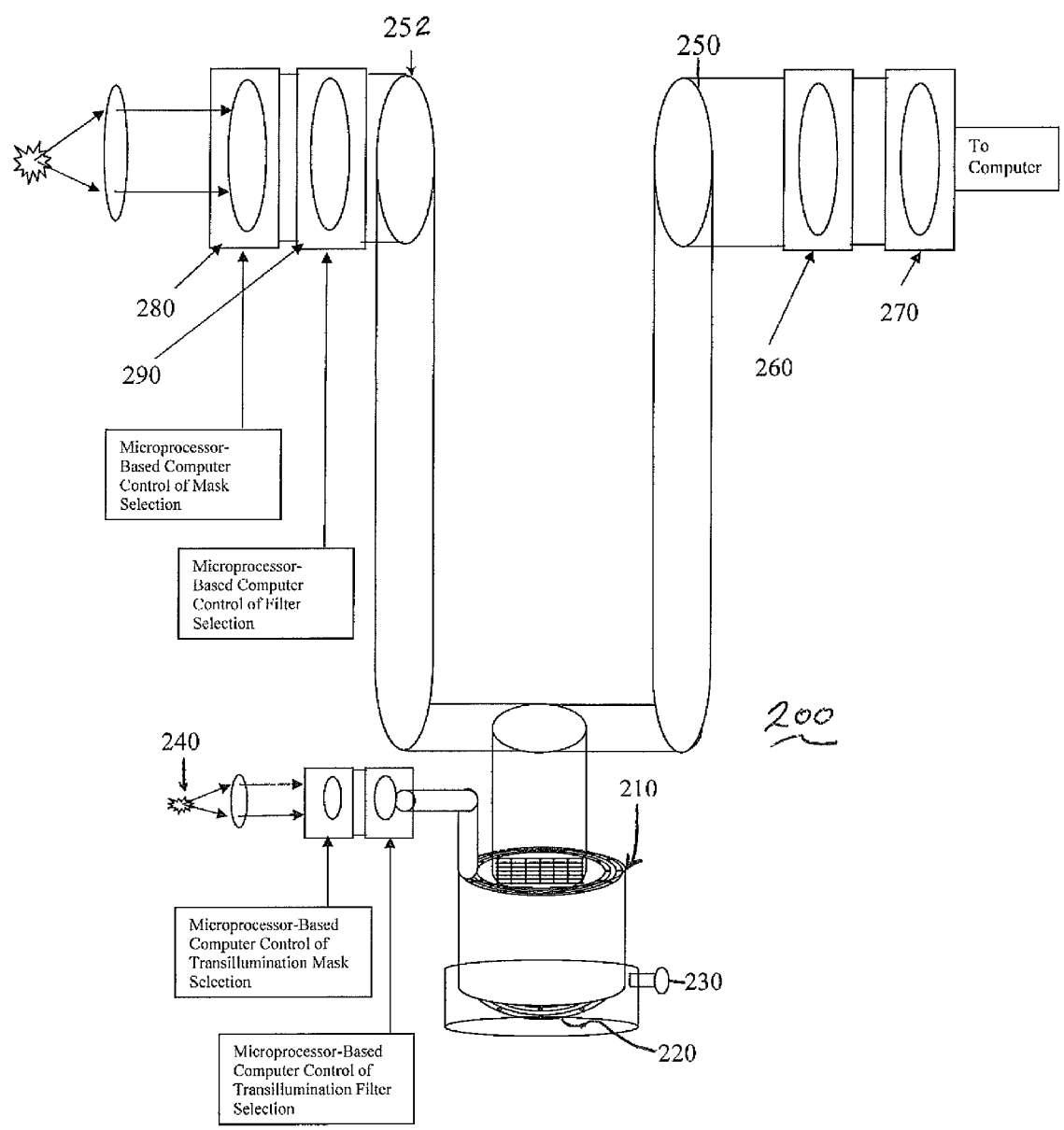

METHOD AND APPARATUS FOR MULTI-SPECTRAL IMAGING AND ANALYSIS OF SKIN LESIONS AND BIOLOGICAL TISSUES

CROSS-REFERENCE TO RELATED APPLICATIONS

This application claims the benefit of U.S. Provisional Patent Application No. 61/088,170, filed Aug. 12, 2008, the entirety of which is incorporated herein by reference.

FIELD OF THE INVENTION

This invention relates to methods and apparatus for imaging and analysis of skin lesions and biological tissues.

BACKGROUND OF THE INVENTION

Skin cancer is a significant health problem in the United States. It has been reported that one of five Americans will get some form of skin cancer in their lifetime. Currently, nearly half of new cancers are diagnosed as skin cancers. Malignant melanoma, the most fatal skin cancer, first forms at the upper layers of skin. When metastasized, cancerous cells from melanoma enter blood vessels and proliferate throughout the body. Malignant melanoma is highly fatal if not detected in early stages. However, it can be cured with nearly 100% survival rate if removed at an early stage.

Physicians usually use the "ABCD" rule to determine if a lesion under investigation is malignant melanoma. The acronym "ABCD" refers to asymmetry, border, color and diameter, respectively. Malignant melanoma typically has an asymmetrical shape, an uneven border, varied colors and a large diameter. Once a suspicious lesion is excised a diagnosis can be confirmed by other instruments. However, neither visual inspection using the "ABCD" rule nor examination of the excised lesion can provide depth information of the skin cancer, which is a crucial signature to grade the degree of invasion of a skin lesion. Angiogenesis, or increased blood flow, plays a very important role in detection of melanomas in early curable stage. Specific patterns of distribution of melanin, oxy-hemoglobin and de-oxy-hemoglobin can lead to characterization of dysplastic nevi and their potential for transformation into malignant melanoma in very early phases.

Various light transportation models have been used by researchers to reconstruct information to characterize skin-lesions. For example, a Kubelka-Munk model was used to simulate the formation of images of melanoma and presented a method to recover blood and melanin distribution in various skin layers. Claridge et al., An inverse method for recovery of tissue parameters from colour images, Information Processing in Medical Imaging. Springer, Berlin, LNCS2732, pp. 306-317. However, the Kubelka-Munk model is theoretically established in a one-dimensional system with point-based measurements. For more complex geometries, Monte Carlo simulation or Diffusion Approximation has been used in optical tomographic modalities for more accurate reconstructions. The commonly adopted strategy for reconstruction involves dividing the field of view into a number of voxels and assuming constant optical properties in each voxel. The optical properties are then estimated voxel-by-voxel by matching model predicted measurements to the actual measurements. This is a typically under-determined and ill-posed inverse problem as the number of measurements is usually much less than the number of voxels to be reconstructed. In general, the forward process is a mapping from high dimensional space (unknown optical properties of voxels) to low dimensional space (limited measurements). Due to the loss of information during the forward process, the solution to the inverse problem is not unique and usually has to be stabilized through various regularization methods. It is therefore difficult to obtain a quantitatively accurate and well-localized solution. In addition, light photons are quickly diffused in a turbid medium such as human skin. As a result, there is a strong dependence or similarity between different measurements such that increasing the number of measurements would not lead to a dramatic change in the characteristic behavior of the inverse problem.

In recent years, optical medical modalities have drawn significant attention from researchers. Visible and near-infrared light wavelengths have been used in surface reflectance, transillumination and transmission based methods. See, Ganster et al., Computer aided recognition of pigmented skin lesions, Melanoma Research, vol. 7 (1997); Seidenari et al., Digital video-microscopy and image analysis with automatic classification for detection of thin melanomas, Melanoma Research 9(2), 163-171 (1999); Menzies et al., Automated instrumentation and diagnosis of invasive melanoma, Melanoma Research vol. 7, 13 (1997); Claridge et al., From color to tissue histology: Physics-based interpretation of images of pigmented skin lesion, Medical Image Analysis, pp. 489-502 (2003); Tomatis et al., Automated melanoma detection: multi-spectral imaging and neural network approach for classification, Med. Phys. 30(2), pp. 212-221 (2003); Tomatis et al., Spectro-photo-metric imaging of subcutaneous pigmented lesion: Discriminant analysis, optical properties and histological characteristics, J. Photochem. Photobiol., B 42, 32-39 (1998). U.S. Pat. No. 5,146,923 discloses a portable nevoscope which provides a noninvasive means to examine a skin lesion in situ, and provides a means to process and analyze skin lesion data relating to properties such as thickness, color, size, pigmentation, boundary, and texture. Due to the limited view and limited-angle measurements available via the prior art nevoscope, the intrinsic ill-posed and under-determined nature of optical imaging pose problems in reconstructing accurate tomographic information.

Consequently there is a need for an improved nevoscope device and methods of obtaining improved reconstruction results.

SUMMARY OF THE INVENTION

In accordance with various aspects of the present invention multispectral imaging systems and methods are provided.

Optical modalities can provide a portable imaging system for routine screening and monitoring of skin-lesions. Multi-spectral optical imaging using visible and infrared light wavelengths as disclosed herein can provide information about physiologically meaningful chromophores such as melanin, oxyhemoglobin and deoxyhemoglobin through utilization of differences in their wavelength dependent absorption and scattering coefficients. The apparatus and methods disclosed herein are generally applicable for optical image reconstruction.

In accordance with one embodiment an improved multi-spectral nevoscope is disclosed providing transillumination for imaging skin lesions for diagnosing malignant melanoma non-invasively. In one embodiment the device comprises substantially a portable optical imaging device that uses specific wavelengths in the visible and infrared spectrum of electromagnetic radiation to transilluminate a skin-lesion or a biological tissue or specimen for imaging and maps multispectral 2-dimensional images into 3-dimensional virtual space for providing 3-D distributions of pre-defined parameters representing the characteristic properties (such as melanin, hemoglobin and deoxyhemoglobin, etc.) of a skin-lesion. These characteristic distributions of specific parameters can be analyzed and used for detection and management of skin-cancers, or characterization of a biological tissue or specimen. The device allows a background transillumination source for excitation or preparation of background tissue such as the surrounding skin of a skin lesion or the entire tissue itself for fluoroscopy imaging.

In accordance with an embodiment the device may include multiple transillumination rings for background tissue preparation or excitation for lesion imaging for optimal penetration and subcutaneous illumination of skin lesions. The device may include multiple adaptive combinations of source and receiver channels distributed over the imaging area through fiber-optics cables, optical illuminators and filters, and computer-controlled image sensors such as CCD arrays. Systems in accordance with the present invention are of critical value to characterize skin lesions and biological tissues for optical and/or molecular imaging and analyses of associated distributions of characteristic parameters. A series of images obtained with multiple excitation and source-illumination geometries with multi-spectral filters may be analyzed by visual inspection/diagnosis and/or 3-D mapping of distribution of specific parameters such as oxyhemoglobin, deoxyhemoglobin and melanin for diagnostic evaluation and characterization of skin lesion or tissue.

The present apparatus may be used for clinical monitoring of skin lesions on patients with high risk of developing malignant melanoma, in addition to monitoring other skin cancers and conditions including those developed from allergic reactions in response to drugs, foods and the like.

In accordance with a further embodiment a shape-based multi-constrained reconstruction algorithm is disclosed which uses genetic algorithm-based optimization methods to find the best possible reconstruction solution. In one embodiment, a skin lesion such as melanoma is modeled as melanin and blood parts, which are delineated by two cubic tensor-product B-spline surfaces. This reduces the number of unknowns to a few control parameters of the surfaces. The parameters are then coded into a genetic algorithm to find a solution through global optimization.

In accordance with a further embodiment a multispectral imaging (MSI) method uses plural selected visible wavelengths for transillumination to acquire multiple remittance images. Different wavelengths of light are projected through fiber-optics-directed ring-light sources for transilluminating the skin lesion through the surrounding skin area for background imaging for calibration, tissue excitation, or tissue preparation for imaging. The entire remittance signature spectrum using multiple light wavelengths improves characterization of skin, dysplastic nevi, melanomas and other skin-lesions. Multiple discrete sources used in sequential imaging of the skin lesion provide extended image data for use in characterizing the skin lesion. This characterization may be based on the visual examination of multispectral transillumination images and/or computer based analysis and three-dimensional reconstruction of the skin lesion.

In accordance with a further embodiment an algorithm is provided in which a skin lesion such as melanoma is modeled as melanin, hemoglobin and deoxyhemoglobin.

BRIEF DESCRIPTION OF THE DRAWINGS

To assist those of ordinary skill in the relevant art in making and using the subject matter hereof, reference is made to the appended drawings, wherein:

FIG. 2 is a schematic diagram of an illumination and imaging system in accordance with at least one embodiment of the present invention;

FIG. 8A reflects double-surface model results (left: first surface, right: second surface) and FIGS. 8B-8E reflect reconstructed surfaces with different constraints in accordance with at least one embodiment of the present invention;

FIG. 10A depicts the first surface and FIG. 10B depicts the second surface;

Figure 1:
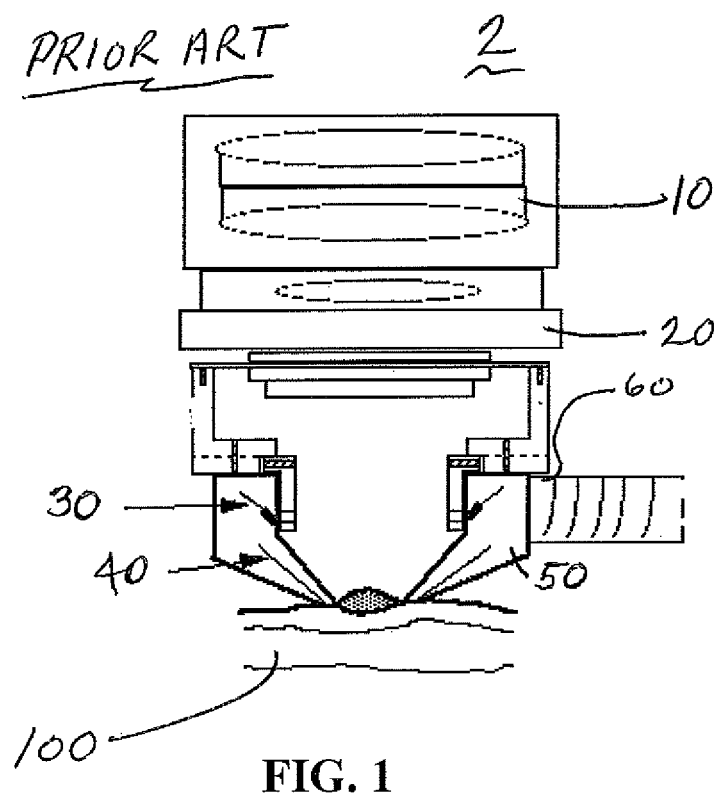
FIG. 1 is a schematic diagram of a prior art nevoscope apparatus.

It should be noted that the appended drawings illustrate only typical embodiments of this invention and are therefore not to be construed as limiting of its scope, for the invention may admit to other equally effective embodiments. Where possible, identical reference numerals have been inserted in the figures to denote identical elements.

DETAILED DESCRIPTION OF THE INVENTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

Now referring to FIG. 1 a schematic of a prior art Nevoscope apparatus 2 employing white light-based transillumination is shown including an optical lens 10, lens mount bracket 20, surface light fibers 30, transillumination fibers 40, a ring light 50 and monocoil 60. As shown the nevoscope is positioned over skin 100.

Now referring to FIG. 2, an embodiment of an improved Nevoscope apparatus 200 is shown. Apparatus 200 includes a housing 210, face plate 220, transillumination outer ring fiber cable 240, main imaging area fiber cables 250 and 252, focusing lens/polarizer 260, image sensor CCD 270, source mask 280 and multispectral filter 290. Source mask 280 and multispectral filter 290 may be rotatable and/or selectable, such as by microprocessor-based computer control. Apparatus 200 may include a transillumination mask and/or filter which may be microprocessor-based computer controlled. A face plate height adjuster 230 such as for epi-illumination may be included in the apparatus 200.

Figure 2A:
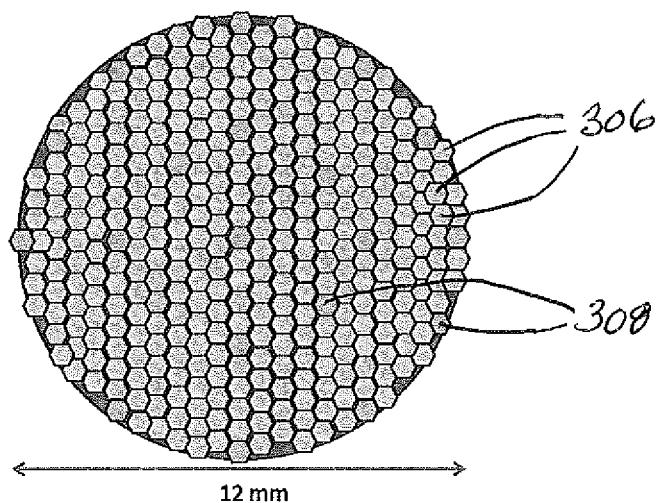
FIG. 2A is a schematic diagram of a layout of contiguous fiber-optics bundles-based imaging geometry, including fiber bundles with receiver channels and illuminating channels with N-to-1 geometry, in accordance with at least one embodiment of the present invention.

Now referring to FIG. 2A, contiguous fiber-optic bundles with receiver channels 306 and illuminating channels 308 with N-to-1 geometry are employed in an alternative nevoscope apparatus. Instead of an incandescent illuminator with a set of filters to produce visible and near-infrared wavelengths, multiple multispectral surface mount light emitting diodes (LED) (such as are commercially available from Lumex Inc.) with an appropriate multiplexed LED driver (such as LTC3219 from Linear Technology) to drive the LEDs can be used. A square pulse signal may be used to turn on the LEDs. A control signal can be used to direct the turn-on time (preferably in the order of a few milliseconds) to a particular LED at a time in a sequential manner. The control and the turn-on signal pulses can be synchronized to the camera frame rate in order to ensure each picture frame corresponds to a single LED illumination.

Fiber optic bundles (such as those made from high quality silica with better than 99% transmission from 450 nm to 960 nm, available through SCHOTT North America) can be used also in a contiguous manner rather than distributed manner for illumination and receiver channels in a particular geometry (such as in alternate mode or N-to-1 mode in which there are N number of receiver channels for each illumination channel; where N is positive integer preferably N=1, 2, . . . 64; when N=1, it becomes the alternate mode).

Fiber optic bundles can be directly divided into illumination and receiver multi-core channels where multi-core illumination channels are connected with multispectral LEDs through multiplexed LED drivers (preferably LTC3219, Linear Technology) and receiver channels are connected to a CCD camera (such as Sony ICX415 CCD ) through a focusing optical lens.

Figure 3:
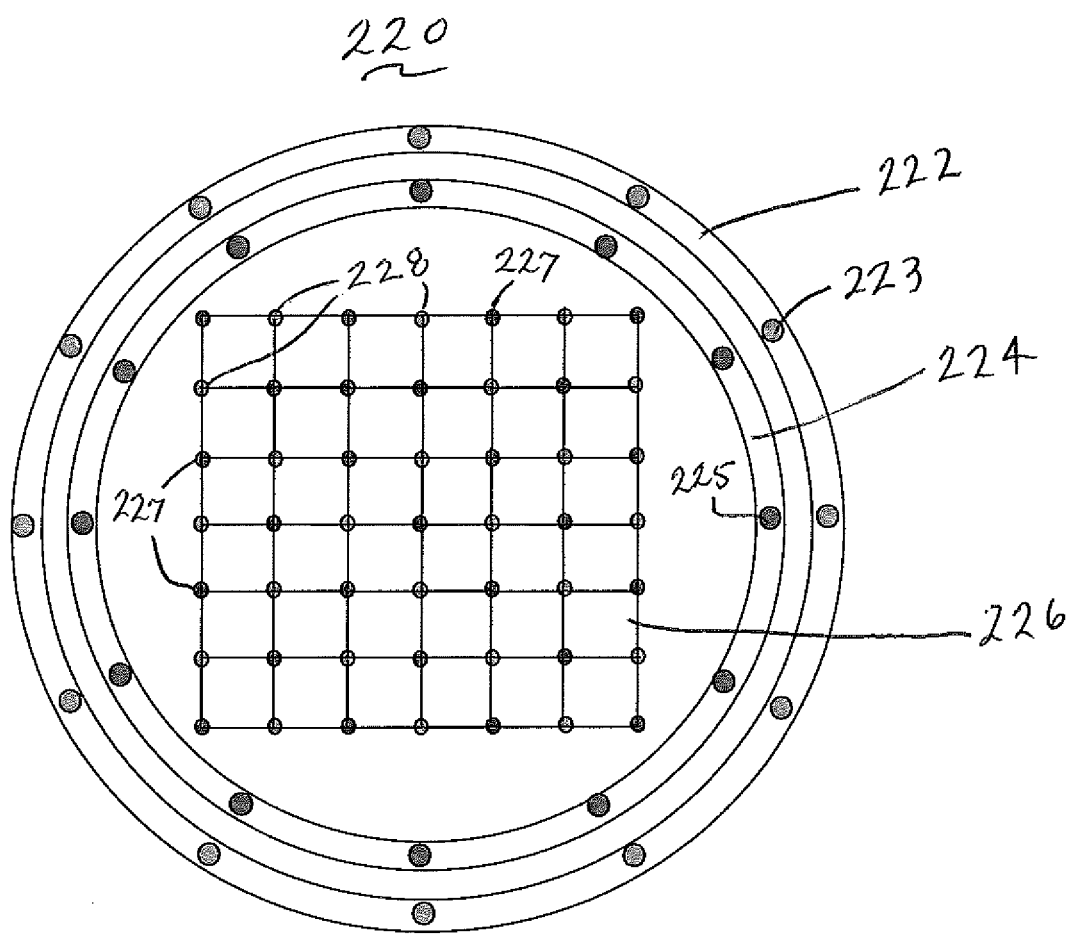
FIG. 3 is a schematic diagram of a sensor face plate in accordance with at least one embodiment of the present invention.

Now referring to FIG. 3, face plate 220 includes outer ring illuminators 222 and 224 and imaging area 226 with distributed sources in alternate positions in a matrix corresponding to the source mask. Outer ring illuminator 222 includes shorter wavelength transillumination fiber channels 223 oriented at 45 degree convergent beam for multispectral or specific wavelength-based background image excitation. Outer ring illuminator 224 includes longer (relative to illuminator 222) wavelength transillumination fiber channels 225 oriented at 45 degree convergent beam for multispectral or specific wavelength-based background image excitation. Imaging area 226 includes plural illumination fiber channels 227 operably connected to an illuminator-filter assembly and plural receiver fiber channels 228 operably connected to the CCD image sensor 270.

Transillumination imaging is achieved through 45 degree convergent beams through fibers distributed along outer ring(s) 222 and 224 as described above with separate illumination, transilumination masks 280 and multispectral filter 290 selection and control. The described transillumination using any selected optical wavelength can be used for tissue excitation such as for fluoroscopy and/or simple transillumination imaging of background skin/medium.

Face plate 220 may be removably attached to housing 210 and is operably connected to a removable lens/polarizer 260 that provides an interface to the imaging areas. The fibers 227 and 228 are distributed over the imaging area in a matrix that can be radially symmetric or rectangular (as shown). The fibers 227 and 228 from the imaging area 226 split into fiber cables 250 and 252 with the same access to imaging area 226.

Now referring to FIG. 2, for imaging a specific imaging mask may be created and used in the illumination path of fiber cable 252. The mask has openings for the desired fibers to be used as source locations to send light into the specimen/skin-tissue 100. As will be apparent to the skilled artisan, many possible schemes for illumination may be employed by fiber placement.

For multi-spectral imaging, any optical filter of a specific wavelength pass or band filter can be used in the illumination pathway of fiber cable 252 and selected through a computer controlled interface.

For recording images, an appropriate mask is used to receive the light from the fibers that are not used for illumination. The received light is passed through a focusing lens/polarizer 260 to a CCD sensor 270 to form images and record measurements. The corresponding receiver mask can be appropriately selected through a computer controlled interface.

Figure 4A:
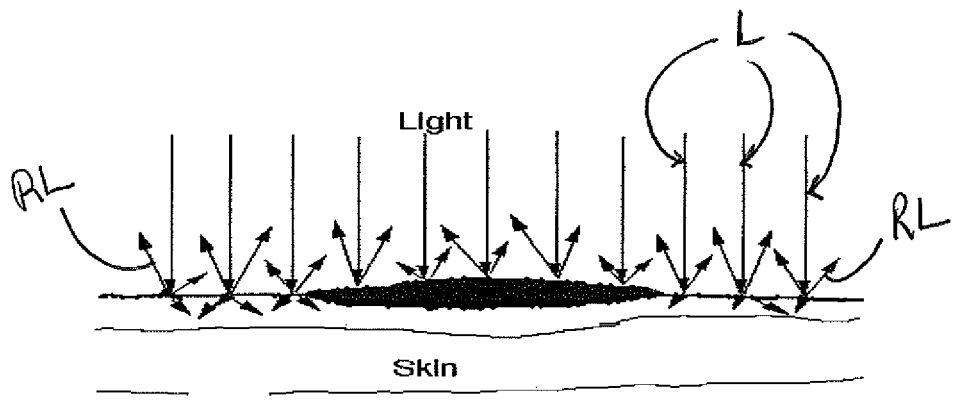
FIG. 4A is a schematic of an epi-illumination mode for the apparatus of FIG. 1.
Figure 4B:
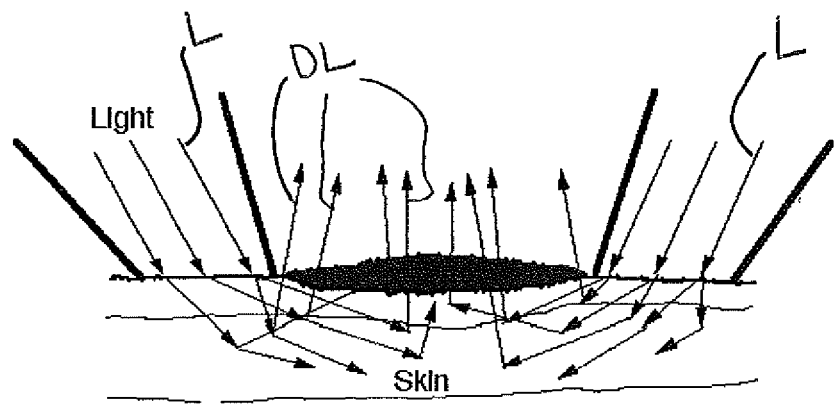
FIG. 4B is a schematic of a trans-illumination imaging mode for the apparatus of FIG. 1.

Now referring to FIG. 4A, in an epi-illumination mode, light beams L are reflected from above the skin surface 100 and diffused reflected light RL is collected by CCD sensor 270 (not shown) through the optical assembly of cross-polarizer and magnifying lens. This image carries apparent characteristic of a lesion that can be used for automatic diagnostic algorithm in terms of the "ABCD" rule. Now referring to FIG. 4B, in a trans-illumination mode, photons of white-light spectrum or a specific wavelength are directed by a transilluminator ring light such as described in FIG. 3 providing an optical interface for light L to enter into the surrounding area of a skin-lesion with a cone-beam making a forty-five degree angle with respect to the normal of skin 100. The back-scattered diffused light DL re-emerges from the skin and captured by the CCD sensor 270 (not shown) such as a camera through the optical assembly. This image contains the information about absorption and scattering properties of the chromophores of underlying skin layers and lesion. Within the optical tomography framework, it is possible to retrieve the distribution of melanin and blood as two key signature variable for early detection of malignant melanoma. In one embodiment, a shape-based multi-constrained algorithm is applied for reconstruction results, which algorithm overcomes the intrinsic problems associated with reconstructing accurate tomographic information.

Figure 5:
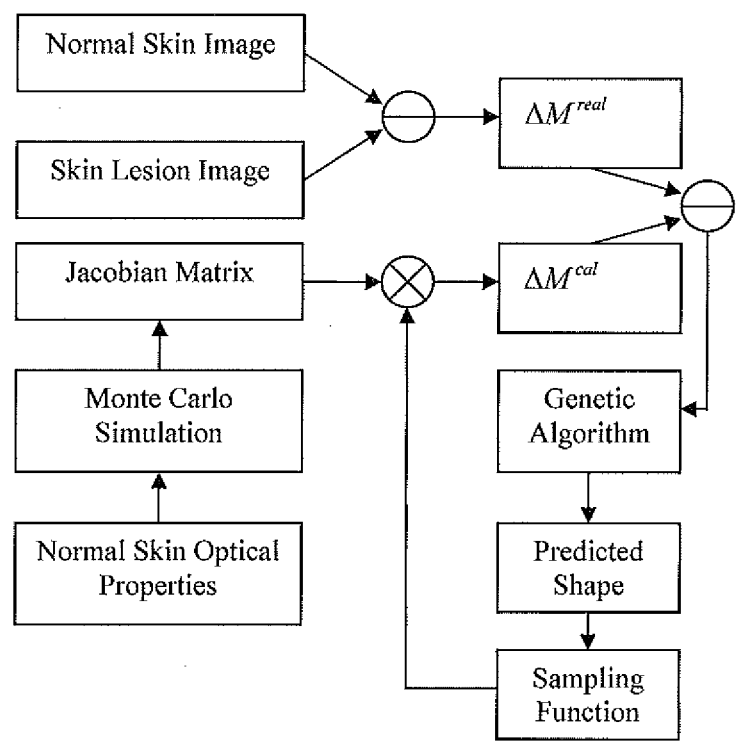
FIG. 5 is a schematic diagram of a method of shape-based reconstruction in accordance with at least one embodiment of the present invention.

Now referring to FIG. 5 a method of reconstruction is described in terms of Nevoscope transillumination images. The method minimizes the difference between the actual ($\Delta M^{real}$) and predicted ($\Delta M^{cal}$); where $\Delta M^{real}$ is the actual measurement vector obtained from multispectral images and $\Delta M^{cal}$ is the computed measurement vector obtained from the reconstructed images. A linearized forward model is adopted and evaluated by Monte Carlo simulation in terms of typical optical properties of normal skin. In one aspect, malignant melanoma is represented by shapes of its melanin part and blood part. These parameters are grouped into genetic algorithms.

To develop a reconstruction strategy, a forward model is required to relate the measurement to the optical properties of tissue under investigation. Regardless of what kind of imaging geometry is used, an optical system may be described as $$M = F(x) \quad (1)$$

where M is the measurement and F is a forward model. x is a distribution of unknown optical properties. Given a reasonable initial guess $x_0$ of the background optical properties, Equation (1) may be expanded into $$M = F(x_0) + F'(x_0)(x - x_0) + \frac{1}{2}F''(x_0)(x - x_0) + \ldots \quad (2)$$

where F' and F" are first order and second order Frechet derivatives respectively.

Let $\Delta M = M - F(x_0)$ and $\Delta x = x - x_0$, Equation (2) may be re-arranged as $$\Delta M = F'\Delta x + \frac{1}{2}F''\Delta x + \ldots \quad (3)$$

The discrete form of Equation (3) turns out to be $$\Delta \vec{M} = J\Delta \vec{x} + \frac{1}{2}H\Delta \vec{x} + \ldots \quad (4)$$

Here, J is the Jacobian matrix and H is the Hessian Matrix.

$$\Delta \vec{M}$$

is the measurement vector and $$\Delta \vec{x}$$

is the vector that gives the variations from the background $$\vec{x}_0.$$

Neglecting higher order terms in Equation (4), a simplified linear system can be expressed as $$\Delta \vec{M} = J\Delta \vec{x} \quad (5)$$

The formulation in terms of Equation (5) leads to linear optical tomography which is also known as "difference imaging" with two measurements. One is for background tissue (that is, $x_0$) and another is for abnormal tissue (that is, unknown x). The difference is then fed to the reconstruction algorithm to obtain the optical properties. In this method, such a linear approach is adopted for nevoscope and the Jacobian matrix is extracted by Monte Carlo simulation.

Monte Carlo (MC) simulation is viewed as the "gold standard" to modeling light transportation and has been extensively used by researchers in optical communities. One of the major types of MC simulations predicts the trajectories of photons in an absorption-free medium then attenuates the weights of photons in terms of microscopic Beer's law. Using this approach, the trajectories of photons can be stored and used repeatedly which speeds up the calculation and absorption properties in the model and can be easily updated. A Monte Carlo procedure based on this approach and tuned to Nevoscope geometry is described as follows.

A nevoscope uses a ring light with radius r and incident angle 45 degree with respect to the normal of skin surface. In the coordinate system used in the experiments that follow, skin surface is represented by x-y plane at z=0 and z axis points inward into the medium. The light source is realized by launching a photon at a random position $(x_0, y_0, 0)$ on the ring, where $$x_0 = r\cos(2\pi\xi) \text{ and } y_0 = r\sin(2\pi\xi) \quad (6)$$

where, $\xi$ is a uniform random number from 0 to 1. Because the discrepancy of refractive indices between air and skin, the photon will change its incident direction which is governed by Snell's law $$n_i \sin(\alpha_i) = n_t \sin(\alpha_t) \quad (7)$$

As the photon loses part of its energy due to specular reflection, considering each photon has normalized energy 1, the remaining energy is given by $$w_0 = 1 - \frac{1}{2}\left[\frac{\sin^2(\alpha_i - \alpha_t)}{\sin^2(\alpha_i + \alpha_t)} + \frac{\tan^2(\alpha_i - \alpha_t)}{\tan^2(\alpha_i + \alpha_t)}\right] \quad (8)$$

For Equations (7) and (8), $\alpha_i = 45°$ is the incident angle and $\alpha_t$ is the transmitted angle. $n_i = 1$ is the refractive index of the ambient and $n_t$ is that of stratum corneum.

After the photon is launched, it undergoes multiple scattering before termination. The probability of path length that a photon would encounter a scattering event is given by Sobol, The Monte Carlo method (Chicago, Ill.: University of Chicago Press), 1974:

$$p(l) = \mu_s \exp(-\mu_s l)\exp(-\mu_a l) + \mu_a \exp(-\mu_a l)\exp(-\mu_s l) \quad (9)$$

To predict the photon trajectory first, absorption may be neglected temporarily. That is, the simulation is done with an absorption free skin model. Thus Equation (9) reduces to $$p(l) = \mu_s \exp(-\mu_s l) \tag{10}$$

So the path length between scattering events is derived as $$l = -\frac{\ln(\xi)}{\mu_s} \tag{11}$$

When a photon completes its one step, it will scatter into a new direction. The direction is characterized by deflection and azimuthal angles. The azimuthal angle is sampled from a uniform distribution from 0 to $2\pi$ but the deflection angle has to be sampled from a phase function which represents the typical forward scattering of biological tissue. A phase function may be expressed as $$p(\cos\theta) = \frac{1}{4\pi} \frac{1-g^2}{(1+g^2-2g\cos\theta)^{\frac{3}{2}}} \tag{12}$$

In addition, it is quite likely that a photon will travel across internal refractive index mismatched interfaces or hit the skin surface during its transportation. If a photon hits the surface, its energy can be separated into two parts: one part escapes the surface and the other part is internally reflected to propagate with reduced energy. The ratio between internal reflected energy and the original energy is given by Fresnel reflection coefficient.

$$R(\alpha_i) = \begin{cases} \frac{(n_t - n_i)^2}{(n_t + n_i)^2} & \text{(if } \alpha_i = 0\text{)} \\ \frac{1}{2}\left[\frac{\sin^2(\alpha_i - \alpha_t)}{\sin^2(\alpha_i + \alpha_t)} + \frac{\tan^2(\alpha_i - \alpha_t)}{\tan^2(\alpha_i + \alpha_t)}\right] & \left(\text{if } 0 < \alpha_i < \sin^{-1}\left(\frac{n_i}{n_t}\right)\right) \\ 1 & \left(\text{if } \sin^{-1}\left(\frac{n_i}{n_t}\right) < \alpha_i < \frac{\pi}{2}\right) \end{cases} \tag{13}$$

In Equation (13), $\alpha_i$ and $\alpha_t$ are angle of incidence and transmittance related by Snell's law. $n_i$ and $n_t$ are medium of incidence and transmittance respectively.

In the case of a photon crossing internal interfaces, the "Russian roulette" approach proposed by Wang et al., MCML-Monte Carlo modeling of light transport in multi-layered tissues, Computer Methods and Programs in Biomedicine 47, 131-146 (1995), may be employed. Once the photon hits an interface, the Fresnel reflection coefficient $R(\alpha_i)$ is calculated and compared to a uniform-distributed random number $\xi$. If $R(\alpha_i) > \xi$, the photon will cross the boundary. Otherwise, it is totally reflected.

Following the rules described above, a photon is launched from the ring source and propagates through the optical skin model until terminated or detected. If its total path length exceeds some preset value, the photon gets terminated. If it is captured by a detector, its energy is re-weighted in terms of its trajectory as $$w_d = (1 - R(\alpha_h)) w_0 \sum_{i=1}^{h-1} R(\alpha_i), \tag{14}$$

where it is assumed the photon hits the skin surface h times during its transportation.

After all trajectories of photons are recorded for a specific detector, the total received intensity is therefore given in terms of microscopic Beer's law $$M = \sum_{i=1}^{p} w_d^i \sum_{j=1}^{q_p} e^{-\mu_a(j)l_j^i} \tag{15}$$

where $w_d^i$ of i th photon is given by equation (14), $\mu_a(j)$ is the absorption coefficient along the path $l_j^i$ of i th photon. It is assumed that the detector received p photons while each of them used $q_p$ steps. The wavelength dependent absorption coefficients are obtained from published data. See, R. Anderson et al., The optics of human skin, Journal of Investigative Dermatology, Vol. 77(1), 13-19 (1981); A. Bashkatov et al., Optical properties of human skin, subcutaneous and mucous tissues in the wavelength range from 400 to 2000 nm, Journal of Physics D: Applied Physics, Vol. 38, 2543-2555 (2005); M. Van Gemert et al., Skin Optics, IEEE Transactions on Biomedical Engineering, Vol. 36(12), 1146-1155 (1989). For purposes of the present experiments a seven-layered skin model is employed which includes stratum corneum (20 µm), epidermis (80 µm), dermis (150 µm), upper blood net dermis (80 µm), reticular dermis (1500 µm), deep blood net dermis (100 µm) and subcutaneous fat (6000 µm). See, I. Meglinski et al., Quantitative assessment of skin layers absorption and skin reflectance spectra simulation in the visible and near-infrared spectral regions, Physiol. Meas, 23, 741-753 (2002).

The absorption coefficient of each layer is a combined effect contributed by several absorbers such as blood, melanin, water and the baseline skin which is free of these absorbers. The absorption coefficient of baseline skin is given by $$\mu_\alpha^{baseline}(\lambda) = 7.84 \times 10^8 \times \lambda^{-3.255} \text{ (cm}^{-1}\text{)} \tag{A.1}$$

Here, $\lambda$ is the wavelength measured in nanometers. The absorption of blood is determined by its oxygenation and fraction of red cells in blood. For example, we assume that haematocrit is Ht % and S % hemoglobin is oxy-hemoglobin. Then the absorption of blood is given as $$\mu_\alpha^{blood}(\lambda) = Ht \times (1-S) \times \mu_\alpha^{Hb}(\lambda) + Ht \times S \times \mu_\alpha^{HbO_2}(\lambda) \tag{A.2}$$

Here $\mu_\alpha^{Hb}(\lambda)$ and $\mu_\alpha^{HbO_2}(\lambda)$ are absorption coefficients of oxy-hemoglobin and deoxy-hemoglobin respectively. The absorption spectra come from compiled data. See, Prahl, Oregon Medical Laser Center, Optical absorption of hemoglobin, omlc.ogi.edu/spectra/hemoglobin/index.html (2006).

The haematocrit has a typical value 45%. The absorption of melanin is given by Meglinski et al.

$$\mu_\alpha^{melanin}(\lambda) = 5 \times 10^{10} \times \lambda^{-3.33} \text{ (cm}^{-1}\text{)} \tag{A.3}$$

In healthy skin, melanin only exists in epidermis layer. Its fraction ranges from 1% to 3% for light skinned Caucasians, from 11% to 16% for well-tanned Caucasians and Mediterraneans, and from 18% to 43% for darkly pigmented Africans. The presence of melanin in deeper skin layers like dermis usually indicates the malignancy of melanoma. The absorption of water is known. Absorption coefficients of two blood free layers stratum corneum and epidermis are predicted by $$\mu_\alpha^{stratum}(\lambda) = ((0.1 - 0.3 \times 10^{-4} \lambda) + 0.125 \mu_\alpha^{baseline}(\lambda))(1 - C_{H_2O}) + C_{H_2O} \mu_\alpha^{H_2O}(\lambda) \tag{A.4}$$

$$\mu_\alpha^{epidermis}(\lambda) = (C_{melanin} \mu_\alpha^{melanin}(\lambda) + C_{H_2O} \mu_\alpha^{H_2O}(\lambda) + (1 - C_{melanin} - C_{H_2O}) \mu_\alpha^{baseline}(\lambda)) \tag{A.5}$$

In the above equations, $C_{melanin}$ is the fraction of melanin in epidermis and $C_{H_2O}$ is the fraction of water in a specific layer. Absorption coefficients of four dermis layers and subcutaneous fat are described by one formula (A.6) while their values depend on how much blood and water they have.

$$\mu_\alpha^{bloodlayer}(\lambda) = C_{blood}\mu_\alpha^{blood}(\lambda) + C_{H_2O}\mu_\alpha^{H_2O} + (1 - C_{blood} - C_{H_2O})\mu_\alpha^{baseline} \quad (A.6)$$

Additional optical properties of skin include scattering coefficients, anisotropy factor and refractive index. Representative values of these optical properties and fractions of absorbers in each skin layer are reported by Meglinski, supra.

Figure 6A:
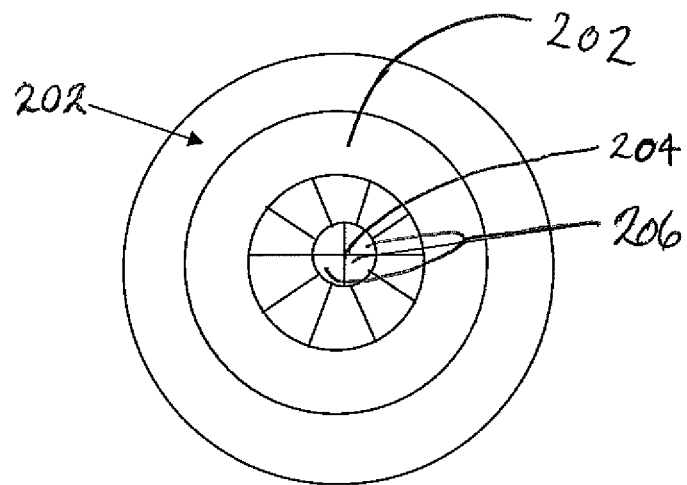
FIG. 6A is a schematic diagram of a discretization strategy of detector space in accordance with at least one embodiment of the present invention.

Now referring to FIG. 6A, in accordance with the experiments, the detector space of the nevoscope is divided into k number of rings 202 (for example, three rings 202 as shown in the FIG. 6A) with equal width. The innermost circle 204 contains four elements or detectors 206 with equal size and other rings 202 are split into a number of elements which maintain the same area as the ones in the innermost circle 204. Using this discretization strategy makes use of the symmetrical geometry of a nevoscope. When evaluating Jacobian matrix, instead of obtaining one MC simulation for each detector, since MC is extremely time-consuming, and noting that all detectors 206 on the same ring actually have similar trajectories, the trajectories for one detector 206 on that ring 202 is recorded and trajectories of other detectors 206 are generated by rotating recorded trajectories. So eventually, only k independent simulations are required to evaluate Jacobian matrix.

Figure 6B:
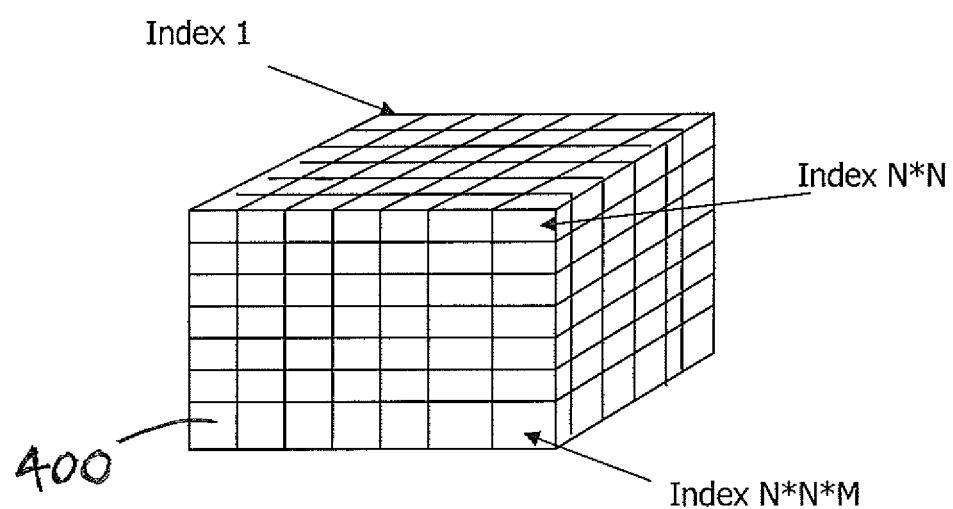
FIG. 6B is a schematic diagram of a discretization strategy of the interrogated tissue medium in accordance with at least one embodiment of the present invention.

Resolution of the reconstructed image is dependent on the size of the Jacobian matrix. Now referring to FIG. 6B, in the experiments, the interrogated volume is divided into N×N×M voxels 300. Each voxel 400 has the size $\Delta x \times \Delta y \times \Delta z$ and has homogeneous absorption coefficient. Where the total number of detectors is T, the measurements of background normal skin is then given by $$M(s) = \sum_{i=1}^{p_s} w_{skin}^j = \sum_{i=1}^{p_s}\left(w_d^j \sum_{j=1}^{N \times N \times M} e^{-\mu_\alpha(j)l_j^i}\right) s = 1, \ldots T \quad (16)$$

where $p_s$ is total number of photons received by the detectors. $l_j^i$ is the path length of photon i in the voxel j. $\mu_\alpha(j)$ is the absorption coefficient of voxel j and is extracted from optical properties of normal skin.

For difference imaging, the Jacobian matrix is given by $$J = \begin{bmatrix} \frac{\partial \Delta M(1)}{\partial \Delta \mu_a(1)} & \frac{\partial \Delta M(1)}{\partial \Delta \mu_a(2)} & \cdots & \frac{\partial \Delta M(1)}{\partial \Delta \mu_a(N \times N \times M)} \\ g & g & & g \\ g & g & & g \\ g & & g & g \\ \frac{\partial \Delta M(T)}{\partial \Delta \mu_a(1)} & \frac{\partial \Delta M(T)}{\partial \Delta \mu_a(2)} & \cdots & \frac{\partial \Delta M(T)}{\partial \Delta \mu_a(N \times N \times M)} \end{bmatrix}_{\Delta \mu_a(j)=0} \quad (17)$$

Each term of Equation (17) is evaluated by recorded photon history. When a tumor grows on the normal skin, variation in measurements $\Delta M(s)$ may be expressed as $$\Delta M(s) = \sum_{i=1}^{p_s}\left(w_{skin}^j \sum_{j=1}^{N \times N \times M} e^{-\Delta \mu_\alpha(j)l_j^i}\right) \quad (18)$$

Taking the derivative with respect to $\Delta \mu_\alpha(j)$ and set $\Delta \mu_\alpha(j)$ to zero results in $$\left.\frac{\partial M(s)}{\partial \Delta \mu_\alpha(j)}\right|_{\Delta \mu_\alpha(j)=0} = \sum_{i=1}^{p_s}(w_{skin}^j \cdot l_j^i) \quad (19)$$

The Jacobian matrix used in the experiments is evaluated on the normal skin model introduced hereinbelow with k=20, N=32 and M=20 which divides the nevoscope detector plane of 1.2 cm diameter into 1588 elements and divides the 1.2 cm×1.2 cm×2000 μm field of view into 32×32×20 voxels.

Inverse Problem

The Equation (5) can be solved by Singular Value Decomposition (SVD), Algebraic Reconstruction Technique (ART), Conjugate Gradient method (CG) and their variants. However, due to the ill-posed and under-determined nature of the inverse problem, it is unlikely to reconstruct quantitatively accurate and well-localized absorption coefficients. Therefore, shape-based optical tomography is preferred, wherein the abnormalities are assumed to have piece-wise constant optical properties in the compact supported regions and the boundaries of these regions can be effectively approximated by some shape functions with the limited numbers of control parameters. As to the reconstruction problem, the unknowns just include a few numbers of control parameters and, sometimes, the piece-wise constant optical properties.

Shape Representation of Malignant Melanoma

A melanoma is essentially a three-dimensional object with distributed pigmentation and chromophores. Malignant melanoma is a result of uncontrolled replication of melasome cells sitting on the basal layer of epidermis. The shape of the melanoma is hence bounded by the epidermis layer. What is needed to describe the lesion is therefore reduced to 2D surfaces in the 3D domain.

Figure 7:
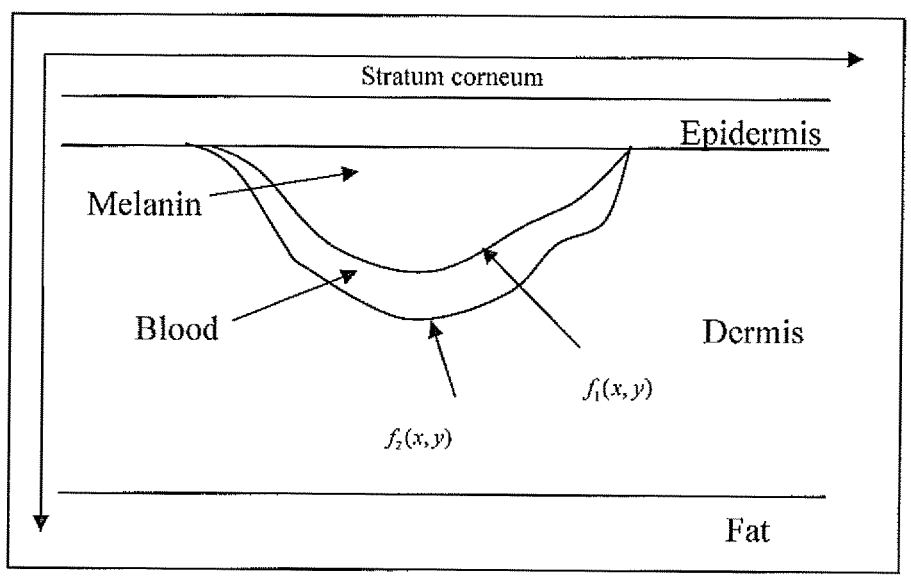
FIG. 7 is a graphical representation of a shape-based model of malignant melanoma in accordance with at least one embodiment of the present invention.

Breaking the malignant melanoma into parts, such as the melanin and the blood parts, permits representation of the malignant melanoma with 2D surfaces. The melanin part is a 3D region bounded by a single surface and the epidermis layer. Within the region, the optical properties are constant and the only absorber is melanin. A second surface which sits below the first surface is used to represent the blood part. The region bounded by the first surface and the second surface is blood only. This model mimics a skin-lesion and its x-z intersection is shown in FIG. 7.

The first surface is represented as $f_1(x, y)$ which corresponds to the depth of lesion from the epidermis layer at the position (x,y). The continuous surface is represented with limited parameters. First, a N×N rectangular grid is positioned to lie over the epidermal layer. Second, the function $f_1(x, y)$ is sampled to N×N discrete values $f_{d1}(X, Y)$. Here, (x, y) is continuous and (X, Y) is N×N numbers of discrete sampling positions. Third, the discrete values are interpolated by the cubic tensor-product B-spline which satisfies the following condition:

$$f_{d1}(X, Y) = \sum_{i=1}^{N} \sum_{j=1}^{N} c_1(i, j)\beta^3(X - i, Y - j) \quad (20)$$

and the original function $f_1(x, y)$ can then be approximated by $$f_{B1}(x, y) = \sum_{i=1}^{N} \sum_{j=1}^{N} c_1(i, j)\beta^3(x - i, y - j) \quad (21)$$

where $$\beta^3(x-i, y-j) = \beta^3(x-i)g\beta^3(y-j) \quad (22)$$

is the tensor product of one-dimensional cubic B-spline basis $\beta^3(x-i)$ and $\beta^3(y-j)$, and $c_1(i, j)$ is B-spline coefficient.

The basis function of B-spline comes from repeated convolution of the box function. It has compact support so that the computation burden is alleviated. The cubic B-spline is continuous up to second derivative which leads to the smoothness of the interpolated surface and in essence puts regularization effect on the reconstructed surface in our shape-based approach. In the end, for the melanin part, the parameters to determine its shape are reduced to N×N discrete values $f_{d1}(X, Y)$ or, equivalently, the corresponding B-spline coefficients $c_1(i, j)$.

Similarly, the second surface can be defined by N×N discrete values $f_{d2}(X, Y)$ or, equivalently, $z_d(X, Y) = f_{d2}(X, Y) - f_{d1}(X, Y)$ which is the thickness of blood region between the first surface and the second surface.

Shape-Based Reconstruction

To reconstruct the surfaces and piecewise constant optical properties, the continuous surface representation should be incorporated into the forward photon transportation model. In our study, the linearized forward model is kept intact but the continuous representation is sampled into the discrete vector of unknowns $$\Delta \overset{r}{x}.$$

That is, $$\Delta \overset{1}{M} = Jg\Delta \overset{r}{x} = JgS(f_{d1}(X, Y), mp1, z_d(X, Y), bp2) \quad (23)$$

where $S(g)$ is the sampling function which converts the continuous shape representation to the voxel-based optical properties in forward model, $mp1$ is the fraction of melanin and $bp2$ is fraction of blood. The inverse problem can therefore be formulated as minimizing the objective function $$F_{obj} = \frac{1}{2}\left\|\Delta \overset{r}{M} - Jg\Delta \overset{r}{x}\right\|^2 = \frac{1}{2}\left\|\Delta \overset{r}{M} - JgS(f_{d1}(X, Y), mp1, z_d(X, Y), bp2)\right\|^2 \quad (24)$$

The unknowns of this inverse problem are reduced to $f_{d1}(x, y)$, $z_d(X, Y)$, $mp1$ and $bp2$. The multi-spectral shape reconstruction using N wavelengths can be formulated as a multi-objective optimization problem and its objective function is given as $$F_{obj} = \alpha_1 g F_{obj}^{\lambda_1} + \alpha_2 g F_{obj}^{\lambda_2} + \ldots + \alpha_N g F_{obj}^{\lambda_N} \quad (25)$$

where, $\{\alpha_1, \alpha_2, \ldots \alpha_N\}$ is a set of coefficients to balance the contributions from different single-wavelength objective functions.

The wavelength dependent objective functions are given as $$F_{obj}^{\lambda_1} = \frac{1}{2}\left\|\Delta \overset{r}{M}^{\lambda_1} - J^{\lambda_1}g\Delta \overset{r}{x}^{\lambda_1}\right\|^2 = \frac{1}{2}\left\|\Delta \overset{r}{M}^{\lambda_1} - J^{\lambda_1}gS^{\lambda_1}(f_{d1}(X, Y), mp1, z_d(X, Y), bp2)\right\|^2 \quad (26)$$

$$F_{obj}^{\lambda_2} = \frac{1}{2}\left\|\Delta \overset{r}{M}^{\lambda_2} - J^{\lambda_2}g\Delta \overset{r}{x}^{\lambda_2}\right\|^2 = \frac{1}{2}\left\|\Delta \overset{r}{M}^{\lambda_2} - J^{\lambda_2}gS^{\lambda_2}(f_{d1}(X, Y), mp1, z_d(X, Y), bp2)\right\|^2$$

$$g$$
$$g$$
$$g$$

$$F_{obj}^{\lambda_N} = \frac{1}{2}\left\|\Delta \overset{r}{M}^{\lambda_N} - J^{\lambda_N}g\Delta \overset{r}{x}^{\lambda_N}\right\|^2 = \frac{1}{2}\left\|\Delta \overset{r}{M}^{\lambda_N} - J^{\lambda_N}gS^{\lambda_N}(f_{d1}(X, Y), mp1, z_d(X, Y), bp2)\right\|^2$$

Various optimization techniques have been reported to solve the shape-based reconstruction problems but all have drawbacks. Hence, a genetic algorithm is used because the gradient need not be evaluated which simplifies the computation and provides reliability. Genetic algorithm is one of the most popular methods used in seeking global minimal. Among the global optimization techniques, genetic algorithm provides a reasonable convergence rate due to its implicit parallel computation. See, Whitely, A Genetic Algorithm Tutorial, Technical Report CS-93-103, Colorado State University (1993); Busetti, Genetic algorithms overview, www.geocities.com/francorbusetti/gaweb; Beasley et al., An overview of genetic algorithms: Part 1, Fundamentals, University Computing, 15(2), 58-69 (1993); Beasley et al., An Overview of Genetic Algorithms: Part 2, Research topics, University Computing, University of Cardiff, 15(4), 170-181 (1993); Ingber et al., Genetic Algorithms and Very Fast Simulated Annealing: Comparison, Mathematical and Computer Modelling 16(11), 87-100 (1992); Goldberg, Genetic Algorithms in Search, Optimization, and Machine Learning, Addison-Wesley Pub. Co. (1989); Houck et al., A Genetic Algorithm for Function Optimization: a Matlab Implementation, NCSU-IE TR 95-09 (1995).

The following is an implementation of the genetic algorithm as it applies to the present invention. As an example, an optimization problem may seek the maximal value of the objective function $$Val = f(\alpha_1, \alpha_2, \alpha_3) \quad (27)$$

This objective function itself is an appropriate fitness function because its value measures how good the solution is. The parameters in the objective function are consequently encoded to the chromosome as genes. It is believed a real number representation is more efficient compared to the binary version. The chromosome with a number of real-numbered genes is given as $$\{\alpha_1, \alpha_2, \alpha_3\} \quad (28)$$

The first step in genetic algorithm is to give an initial population with a number of individuals (that is, with different chromosomes) to reflect the variety. This population is usually generated randomly. This step in fact means to randomly sample the parameter space. Different from random searching technique, the genetic algorithm realizes implicit parallel computation so that it has a faster convergence rate. In terms of schema theory, the fitness of an individual not only represents its optimality at that specific position but gives fitness of some underlying pattern known as schema. After the population has been initialized, the fitness score of each individual is evaluated to facilitate the reproduction step.

Reproduction reflects the natural reality that better fitted individuals have higher probabilities to appear in the next generation. Given the fitness scores of individuals, the next generation is selected in terms of several selection rules. A common method is to select the next generation through the "Roulette Wheel" rule. If the individual i has the fitness score $Val_i$, then its probability to be selected into next generation is given as $$P = \frac{Val_i}{\overline{Val}} \quad (29)$$

where $\overline{Val}$ is the average fitness of the population with M individuals $$\overline{Val} = \frac{\sum_{i=1}^{M} Val_i}{M} \quad (30)$$

The selection process can be viewed as putting the individuals on a wheel and each individual occupies a pie representing its probability. Randomly selecting M individuals from the wheel results in the next generation.

Crossover is the process that one offspring is generated by two parents. The offspring could become a worse-fitted individual. However, there is a good chance that the offspring has better fitness than both of its parents. Crossover is believed to be the major operator that makes the genetic algorithm have the capability to investigate the parameter space efficiently. One special and efficient real crossover operator is the mathematical crossover and is defined as $$\{\alpha_1^1, \alpha_2^1, \alpha_3^1\} \Rightarrow \quad (31)$$
$$\{p \cdot \alpha_1^1 + (1-p) \cdot \alpha_1^2, p \cdot \alpha_2^1 + (1-p) \cdot \alpha_2^2, p \cdot \alpha_3^1 + (1-p) \cdot \alpha_3^2\}$$
$$\{\alpha_1^2, \alpha_2^2, \alpha_3^2\} \Rightarrow \{(1-p) \cdot \alpha_1^1 + p \cdot \alpha_1^2,$$
$$(1-p) \cdot \alpha_2^1 + p \cdot \alpha_2^2, (1-p) \cdot \alpha_3^1 + p \cdot \alpha_3^2\}$$

where p is a uniform random number from zero to one.

Mutation is another operator to change the chromosome of an individual. It gives each gene in the chromosome a small probability to be set to a random number. This operator gives any region in the parameter space some probability to be investigated. It therefore helps to escape the local minima. However, over-emphasis on the mutation operator leads to a stochastic random search.

Starting from the initial population and going over one generation after another, finally the genetic algorithm converges to the optimal solution. As to the optimization problem occurred in shape-based reconstruction, the objective function is selected as the fitness function. Its parameters is coded into chromosome as $$\begin{Bmatrix} f_{d1}(X_1, Y_1) - f_{d1}(X_2, Y_2) - \ldots - f_{d1}(X_{N \times N}, Y_{N \times N}) - mp1 - \\ z(X_1, Y_1) - z(X_2, Y_2) - \ldots - z(X_{N \times N}, Y_{N \times N}) - bp2 \end{Bmatrix} \quad (32)$$

Reasonable constraints are added to the parameters in preparation of the optimization algorithm. First, the region of support of the lesion in x-y plane is readily available in terms of the epi-illumination nevoscope image (FIG. 4A). This further reduces the number of parameters to represent a surface from N×N to a smaller set. As a consequence, the optimization algorithm has a faster convergence rate. Second, the blood region typically comprises thin layers within a few hundreds of micrometers which put a constraint on z(X, Y). Third, the fractions of melanin and blood are not free parameters. They can also be bounded according to the appearance of melanoma and the clinical experience. Last, multi-spectral imaging provides implicit constraints. Due to the distinct absorption spectra of blood and melanin, a reasonable solution must also satisfy the measurements of all involved wavelengths.

In summary, the method of solving the shape-based reconstruction problem using genetic algorithm to involves the following steps:

Step 1: Initialize the population. The values of genes are randomly generated as well as subject to some specific constraints. The size of the population is sufficient large to reflect randomness.

Step 2: Evaluate the fitness. Each chromosome in the population is evaluated in terms of the objective function and, as a result, associated with a fitness score. This step implicitly includes sampling the shape-representation to fill into the forward model.

Step 3: Evolve the population. This step includes reproduction in terms of the fitness score, arithmetic crossover and mutation.

Step 4: Check the termination condition. The termination condition in the experiment is the number of iterations of the algorithm. Once it exceeds the pre-defined number, the algorithm stops. Otherwise, it returns to step 2 and continues to evolve.

Experiments/Results

To validate the shape-based multi-spectral algorithm, a double-surface model was created to represent malignant melanoma. The first and second surfaces are described by a mixed Gaussian function which are given as $$f_1(x, y) = \text{MAX}(peak1gG(x, y, \mu_{1a}, \mu_{2a}, \sigma_a), \quad (33)$$
$$peak2gG(x, y, \mu_{1b}, \mu_{2b}, \sigma_b))$$

-continued $$f_2(x, y) = \text{MAX}(peak3gG(x, y, \mu_{1a}, \mu_{2a}, \sigma_a),$$
$$peak4gG(x, y, \mu_{1b}, \mu_{2b}, \sigma_b))$$

where the Gaussian function is $$G(x, y, \mu_1, \mu_2, \sigma) = \frac{1}{2\pi\sigma^2}\exp\left(-\frac{(x-\mu_1)^2 + (y-\mu_2)^2}{2\sigma^2}\right) \quad (34)$$

The parameters used in Equation (33) are $$\begin{cases} \mu_{1a} = 0.0375 \times 2 & \text{cm} & \mu_{2a} = -0.0375 \times 3 & \text{cm} \\ \mu_{1b} = -0.0375 \times 2 & \text{cm} & \mu_{2b} = 0.0375 \times 3 & \text{cm} \\ \sigma_a = 0.0375 \times 2.5 & \text{cm} & \sigma_b = 0.0375 \times 2 & \text{cm} \\ peak1 = 100 \times 6 & \mu m & peak2 = 100 \times 4 & \mu m \\ peak3 = 100 \times 8 & \mu m & peak4 = 100 \times 6 & \mu m \end{cases} \quad (35)$$

Figure 8A:
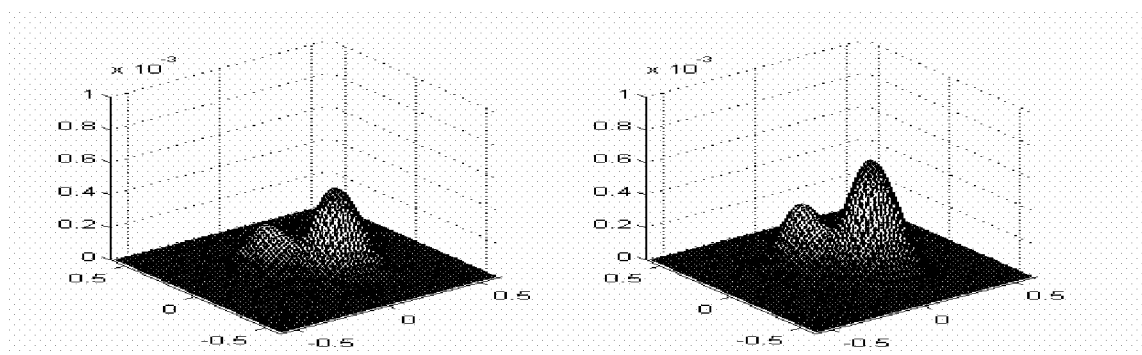
FIGS. 8A-8E are graphical depictions of reconstruction results.
Figure 8B:
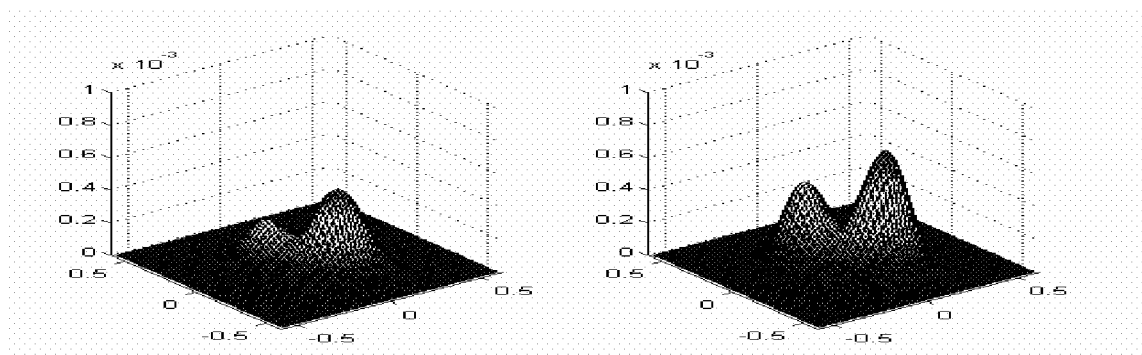
Figure 8C:
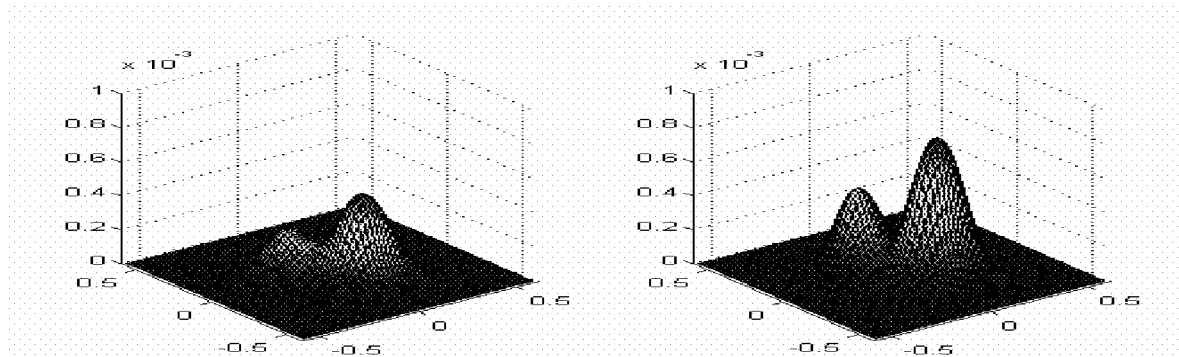
Figure 8D:
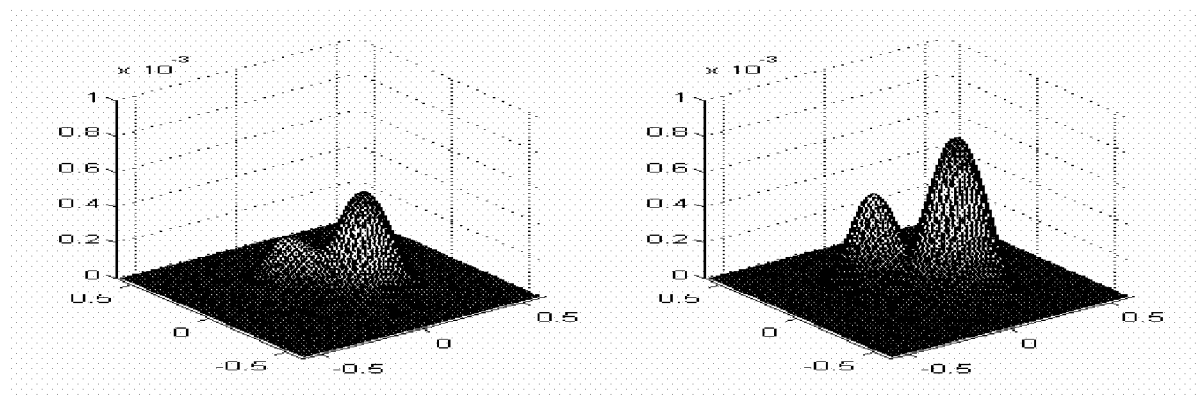
Figure 8E:
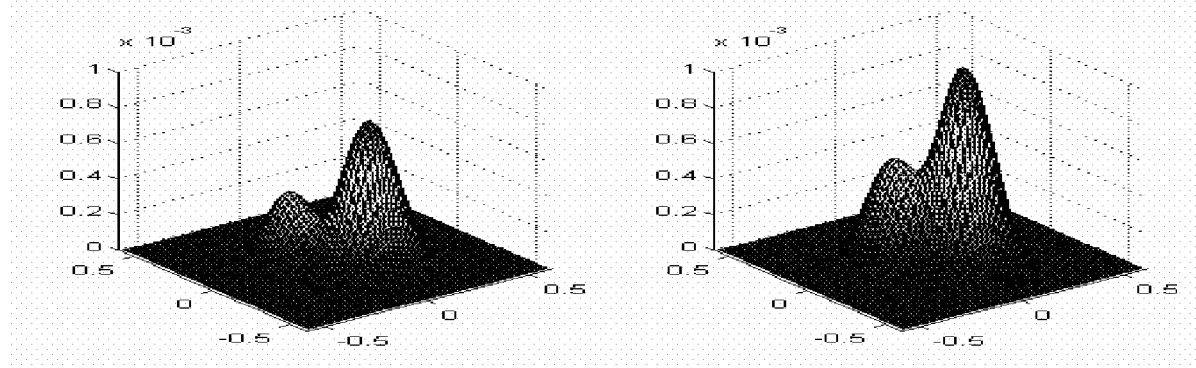

The fraction of melanin is set to 5% between the epidermal layer and the first surface $f_1(x, y)$. The fraction of blood is set to 20% between the first surface $f_1(x, y)$ and the second surface $f_2(x, y)$. This model has sufficient variation in order to verify the reliability of the reconstruction algorithm. FIG. 8A displays the 3D view of this model.

The double-surface continuous model is sampled and two measurements $\Delta M^{580}$ and $\Delta M^{800}$ are calculated by Monte Carlo simulation at 580 nm and 800 nm respectively. Next a 9×9 rectangular grid is overlapped on the epidermal layer. The region of support of the lesion is counted as 10 discrete control points. As a result, the chromosome contains 22 genes and is coded as $$\begin{cases} f_{d1}(X_1, Y_1) - f_{d1}(X_2, Y_2) - \ldots - f_{d1}(X_{10}, Y_{10}) - mp1 - \\ z(X_1, Y_1) - z(X_2, Y_2) - \ldots - z(X_{10}, Y_{10}) - bp2 \end{cases} \quad (36)$$

The fitness function of the genetic algorithm is given as $$F_{obj} = \alpha_1 g F_{obj}^{580} + \alpha_2 g F_{obj}^{800} \quad (37)$$

where $\alpha_1$ and $\alpha_2$ can be chosen on the relative weight assigned to melanin contents to the entire volume. About 30% of the entire volume to be pigmented and used $\alpha_1 = 0.3$ and $\alpha_2 = 1$ was considered in the experiment.

Four simulations with different constraints were implemented in real number presented genetic algorithm. Results are summarized in Table 1. The recovered surfaces are displayed in FIG. 8B-E. In each case, the left is the first surface and the right is the second surface. There is no constraint for the first surface while the thickness between the first surface and the second surface is set to be 300 µm to represent a thin layer of blood net.

Figure 9:
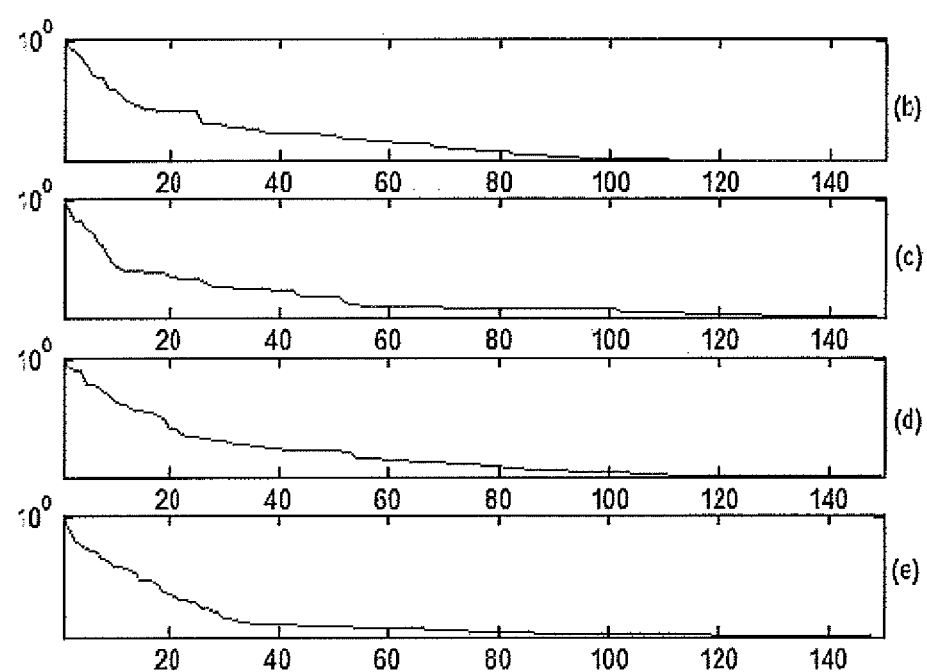
FIG. 9 is a graphical depiction of convergence analysis of the genetic algorithm with various constraints in accordance with at least one embodiment of the present invention.
Figure 10A:
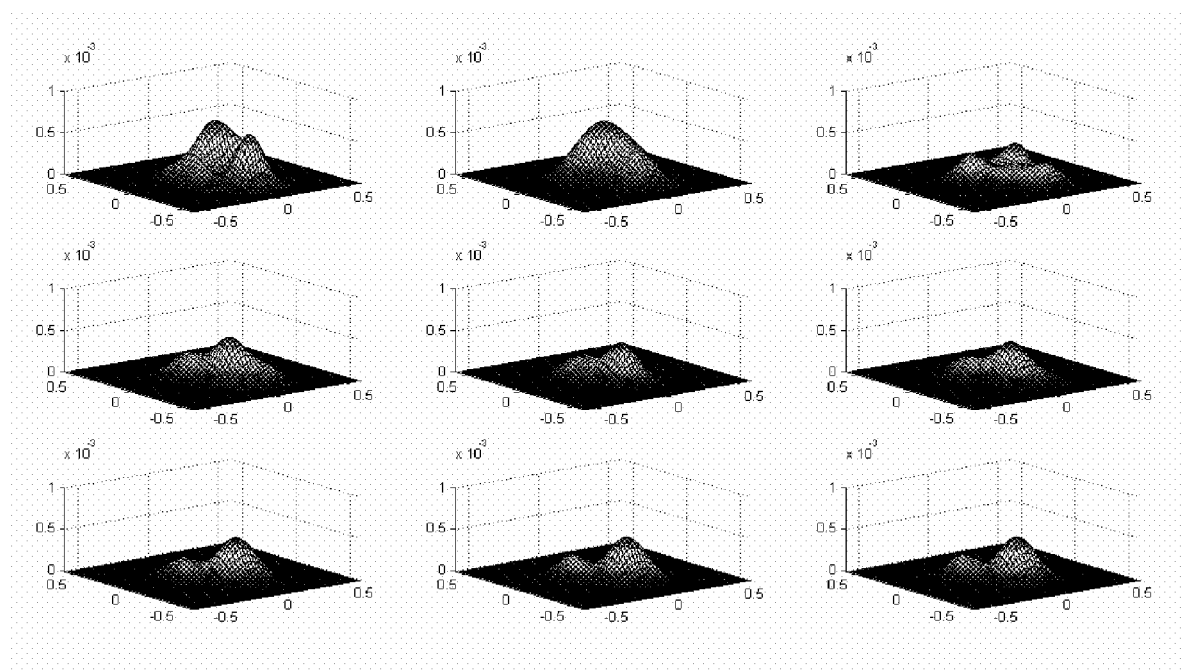
FIGS. 10A and 10B are graphical depictions of a deformation process during optimization in accordance with at least one embodiment of the present invention (from left to right row-wise and top to bottom column-wise)
Figure 10B:
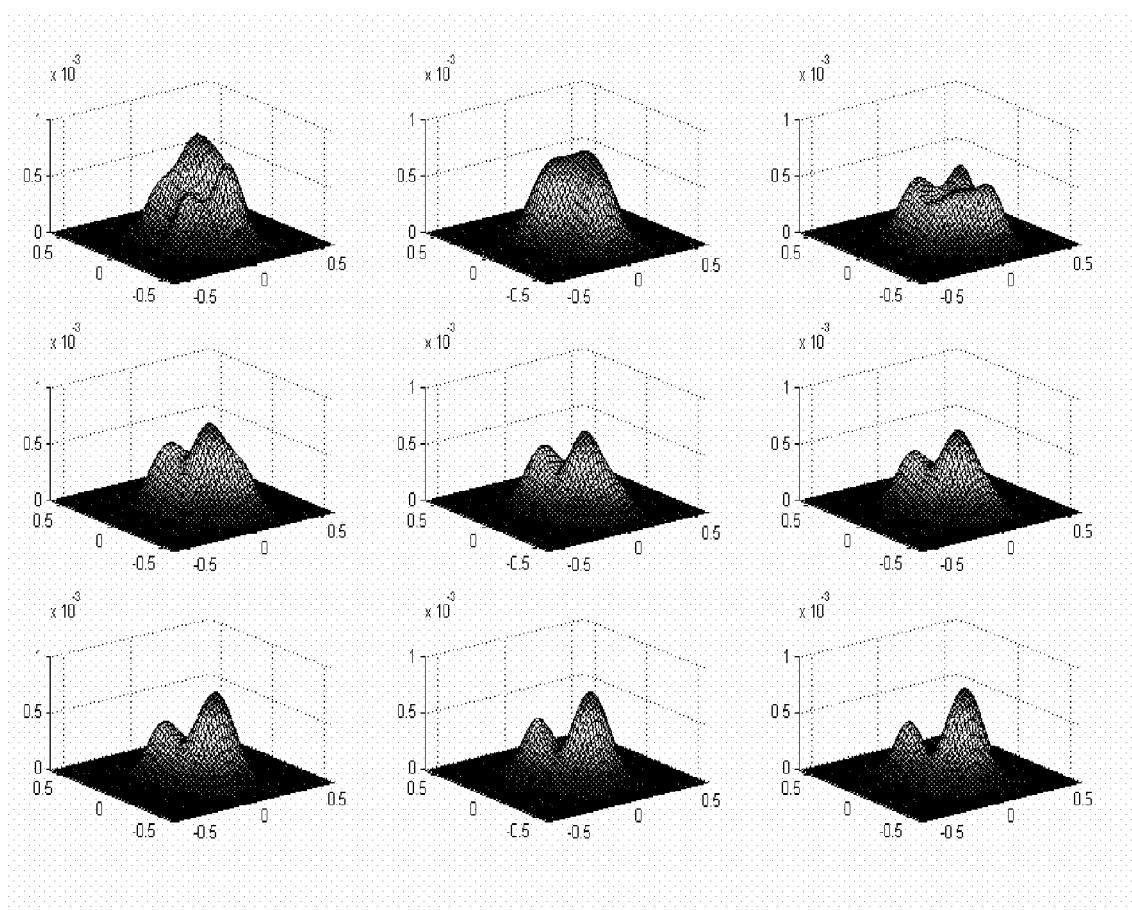

In an example there are 100 individuals in a population and the genetic algorithm terminates after 150 iterations. Now referring to FIG. 9, the fitness scores are normalized and displayed with respect to the number of iteration. As can be seen the genetic algorithm converges in all cases. Now referring to FIGS. 10A and 10B, the deformation process is shown, suggesting that the genetic algorithm has successfully recovered both surfaces.

To further evaluate the reconstruction result, volume deviations Volerr1 and Volerr2 were introduced. They are defined as $$\text{Volerr1} = \frac{|vol1_c - vol1_m|}{vol1_m} \quad (38)$$

where $vol1_c$ is the calculated volume bounded by the first surface and $vol1_m$ is the corresponding volume from the model and $$\text{Volerr2} = \frac{|vol2_c - vol2_m|}{vol2_m} \quad (39)$$

where, $vol2_c$ is the calculated volume bounded by the first and second surfaces and $vol2_m$ is the corresponding volume from the model.

TABLE 1

Summary of Reconstruction Results

| Case | Melanin Bounds (%) | Blood Bounds (%) | Recovered Melanin (%) | Recovered blood (%) | Volerr1 (%) | Volerr2 (%) |
|---|---|---|---|---|---|---|
| (b) | 5-5 | 20-20 | 5 | 20 | 2.68 | 16.58 |
| (c) | 4.5-5.5 | 10-30 | 5.10 | 18.33 | 3.81 | 20.89 |
| (d) | 4-6 | 10-30 | 4.64 | 18.97 | 5.18 | 24.71 |
| (e) | 3-7 | 10-30 | 3.37 | 10.08 | 44.09 | 63.50 |

As shown in Table 1, the constraints have significant impacts on the reconstructed surfaces. Except the loosest constrained case (e), all cases present reasonable reconstructions which are consistent with the model. Moreover, the reconstructed first surface has a smaller volume error than the second surface. There are several reasons to explain the larger volume error of the second surface. First, the absorption coefficient of blood is smaller than that of melanin. As a result, the change in blood region has less contribution to the fitness function. Second, since a reflectance geometry is adopted in the nevoscope, the sensitivity decreases at deeper layers. This also influences the accurate reconstruction of the second surface. Third, because the two surfaces are attached together, the error resulting from the first surface would inevitably propagate to the second surface.

The inventive reconstruction techniques are shown to be a good solution to the ill-posed inverse problem. Using additional wavelengths increases the ability to isolate the true solution from a number of possible solutions.

Monte-Carlo Simulation-Based Mapping of Multispectral Image Information onto a 3-D Volume.

Figure 11:
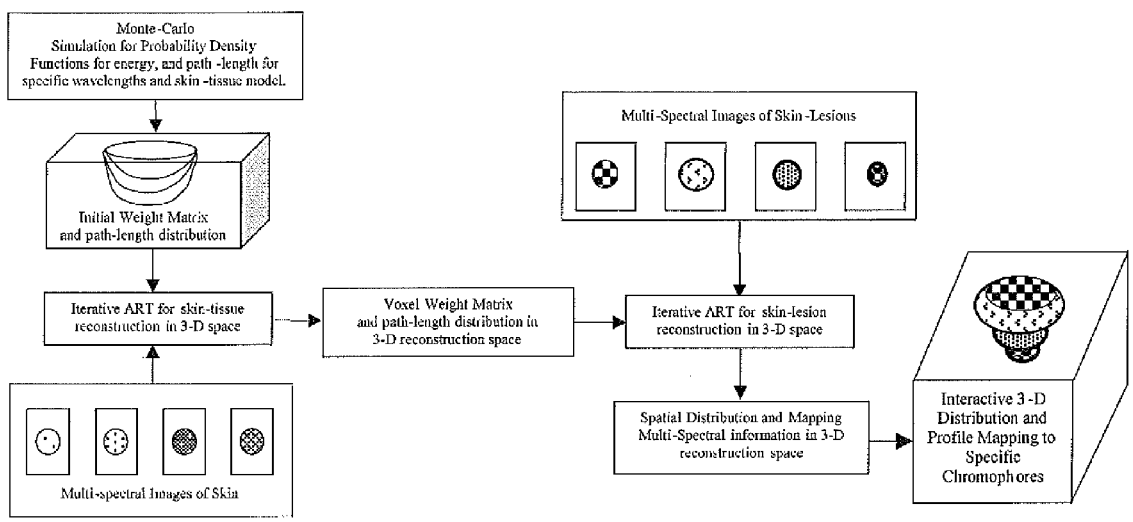
FIG. 11 is a schematic diagram of a 3-dimensional feature reconstruction from multispectral images in accordance with at least one embodiment of the present invention.

Now referring to FIG. 11, in another embodiment a Monte-Carlo simulation-based mapping of multispectral image information onto a 3-D volume is provided. The multispectral image information obtained can be projected onto a 3-D discrete reconstruction volume through the knowledge-based model derived from a Monte-Carlo simulation providing probability distribution functions of energy and path length and energy in the 3-D sub-surface space. The Monte-Carlo simulation of the skin-tissue model (without the lesion) provides a probability distribution of each photon path between the source and detector in the simulated medium. An iterative ART algorithm can be used to employ this matrix of initial weights and path-length information to compute the diffused reflectance distribution that is compared with the acquired multispectral images of skin of the human subjects (near the skin-lesion). Thus, the weights and path-length information of the reconstruction space of the skin is updated using an Algebraic Reconstruction Technique (ART) (See, S. Srinath Maganti, "Three-Dimensional Optical Tomographic Image Reconstruction from Nevoscope Images", Ph.D. Dissertation, Advisor: Atam P. Dhawan, University of Cincinnati (1997); S. Maganti and A. P. Dhawan, "3-D Nevoscope image reconstruction using diverging ray ART", Proceedings SPIE International Conference on Biomedical Optics (1997)) for minimization of the error between the computed diffused reflectance and acquired multispectral images of skin. This updated weight matrix and path-length information in the 3-D reconstruction space now serves as initial weight matrix for reconstructing the skin-lesion information from multispectral images of the skin-lesion using the iterative ART. Thus, Monte Carlo simulation provides the forward model of imaging for the voxel weights and path-length information which is then used in reconstruction through an iterative Algebraic Reconstruction Technique (ART) (See, S. Srinath Maganti, "Three-Dimensional Optical Tomographic Image Reconstruction from Nevoscope Images", Ph.D. Dissertation, Advisor: Atam P. Dhawan, University of Cincinnati (1997); S. Maganti and A. P. Dhawan, "3-D Nevoscope image reconstruction using diverging ray ART", Proceedings SPIE International Conference on Biomedical Optics (1997)) as depicted in FIG. 11.

EXAMPLE

It is assumed a skin lesion property (such as melanin, hemoglobin, or de-oxy-hemoglobin concentration) is represented by $F_i(x,y,z)$; $i=1, \ldots, I$ where I is the number of skin-lesion properties. It is also assumed that the Monte-Carlo simulation and iterative ART-based reconstruction of skin provides the updated initial weight matrix with 3-D distributions of photon energy density represented by $E_j(\alpha, \beta, \gamma)$ with path lengths $P_{k,i,j}((\alpha_l, \beta_m, \gamma_n)^0, E_{j;lmn}), (\alpha_l, \beta_m, \gamma_n)^1, E_{j;lmn}), \ldots, (\alpha_l, \beta_m, \gamma_n)^Z, E_{j;lmn})); k=1, \ldots, K$ where K is the number of paths between source and detector for a specific imaging wavelength j ($j=1, \ldots, J$) for imaging the skin-lesion property $F_i(x,y,z)$. Each path length is a list of voxel coordinates $(\alpha_l, \beta_m, \gamma_n)^z$; $z=1, \ldots, Z$ (where Z is the number of voxels between source and detector) with their respective associated energy level $E_{j;lmn}$. The normalized probability distribution of photon energy provides initial weights for reconstructing the object information $F_i(x,y,z)$ as $RF_i(x',y',z')$ where $RF_i$ is the respective reconstructed property in the 3-D reconstruction space $(x',y',z')$. Let NEVO_TRANS function describe the imaging the skin-lesion property, $F_i(x,y,z)$ through Nevoscope Transillumination with the forward model:

$$[M_j(\alpha,\beta,\gamma)]=NEVO\_TRANS\{F_i(x,y,z)\}=[F_i(x,y,z)].[W_j(\alpha,\beta,\gamma)]$$

where $[M_j(\alpha,\beta,\gamma)]$ is the measured or acquired image, $[W_j(\alpha,\beta,\gamma)]$ is the updated weight matrix, which is approximated and modeled through Monte-Carlo simulation with $[E_j(\alpha,\beta,\gamma)]$.

The objective of the reconstruction process is to obtain an estimate $RF_i(x',y',z')$ of the object property $F_i(x,y,z)$. The ART algorithm starts projecting the acquired image data onto the reconstruction space of voxels using the initial weights and path length information obtained from the Monte-Carlo simulation (forward model). In each iteration, the voxel weight and path length information is used to assign new weight values such that the error between the reconstructed diffused reflectance output from the medium using the new voxel weights and the acquired image is minimized. Thus, the reconstruction process concludes that the incident photon energy radiation on the reconstructed object provides the diffused reflectance output as close as possible to the acquired image as $$[RF_j(x',y',z')]=[P_{k,i,j}((\alpha_l,\beta_m,\gamma_n)^0, E_{j;lmn}), (\alpha_l,\beta_m,\gamma_n)^1, E_{j;lmn}), \ldots, (\alpha_l,\beta_m,\gamma_n)^Z, E_{j;lmn}))]^{INV}. [M_j(\alpha,\beta,\gamma)]=[W_j(\alpha,\beta,\gamma)]^{INV}.[M_j(\alpha,\beta,\gamma)]$$

Thus, through the ART reconstruction process an inverse of the weight matrix, $[W_j(\alpha,\beta,\gamma)]^{INV}$ is obtained through the iterative process. However, since the matrix is very large to invert, the convergence can be obtained using a hierarchical partitioning. Also, the a priori knowledge of the path length from the Monte-Carlo simulation can be used to reduce the size of the sub-matrices to be inverted. Thus, the assignment of the acquired image data onto a reconstructed 3-D space can be efficiently performed for each property of the skin-lesion through specific wavelength based imaging. Thus, the individual wavelength based reconstruction from each of the acquired multispectral images will be obtained. The specific property—(such as melanin, hemoglobin, etc.) based 3-D reconstructed distributions would be obtained through combining the multispectral reconstructions weighted by their respective volume fraction model described in the equations above. The total melanin fraction would be obtained from multispectral images as $$[RF_{melanin}(x', y', z')] = \sum_{j=1}^{J} (f_{j,epmel} + f_{j,pmel} + f_{j,rmel})[RF_j(x', y', z')]$$

$$[RF_{oxy-hemo}(x', y', z')] = \sum_{j=1}^{J} (f_{j,poxy} + f_{j,roxy})[RF_j(x', y', z')]$$

$$[RF_{de-oxy-hemo}(x', y', z')] = \sum_{j=1}^{J} (f_{j,pdeoxy} + f_{j,rdeoxy})[RF_j(x', y', z')]$$

where $f_{j,epmel}$, $f_{j,pmel}$, and $f_{j,rmel}$, are the wavelength dependent volume fractions of melanin in, respectively, epidermis, papillary dermis and reticular dermis; and $f_{j,poxy}$, $f_{j,roxy}$, $f_{j,pdeoxy}$, and $f_{j,rdeoxy}$ are the wavelength dependent volume fractions of oxy-hemoglobin and de-oxy-hemoglobin in, respectively, papillary dermis and reticular dermis. Validation of the melanin and blood-flow volume information can be compared with the pathology for test cases for validation.

Experiments

Different visible light and near-infrared wavelengths in the range of 400 nm 1000 nm (preferably 500 nm to 960 nm) may be used to obtain diffused reflectance-based absorption measurements with different levels of depth of penetration to estimate volumes of selected chromophores such as melanin, oxy-hemoglobin and de-oxy-hemoglobin. A summary of the depth of penetration and characteristic absorption to chromorphores of interest is provided in Table 2.

TABLE 2

Specific light wavelengths and their properties for use in multispectral skin imaging.

| Wavelength | Optical Properties in Skin |
|---|---|
| 405 nm | Superficial penetration (<0.5 mm), used in fluorescence excitation of ALA. High melanin absorption. |
| 470 nm | Superficial penetration (<1.0 mm), used in fluorescence excitation of fluorescein, highly absorbed in melanin. Excellent for imaging superficial melanin associated with sun damage. |
| 500 nm | Superficial penetration (<1.2 mm), used for fluorescence imaging |
| 520 nm | Some fluorescence imaging (<1.5 mm penetration), |
| 560 nm | Superficial penetration (<1.8 mm), highly absorbed by de-oxy-hemoglobin. Highlights superficial blood vessels. |
| 580 nm | Deeper penetration in tissue (<2.3 mm), excellent for imaging most pigmented lesions without interference from the superficial melanin, peak for oxy-hemoglobin absorption. |
| 610 nm | Deeper penetration in tissue (<2.5 mm), excellent for contrast imaging deoxygenated hemoglobin and veins due to large difference in absorption for oxy and de-oxy-hemoglobin. |
| 660 nm | Deep penetration in tissue (>3.0 mm), shows deep pigmentation; large difference in absorption for oxy and de-oxy-hemoglobin. |
| 760 nm | Very deep penetration in tissue, peak for de-oxy-hemoglobin and water absorption. |
| 800 nm | Very Deep penetration, almost equal absorption for de-oxy and oxy-hemoglobin. |
| 910 nm | Very Deep penetration in tissue, peak for oxy-hemoglobin absorption. |

Optical wavelength of 560 nm provides superficial penetration (<1.8 mm) with high absorption by deoxy-hemoglobin and is suitable for imaging superficial blood vessels. While 610 nm wavelength provide deeper penetration in tissue (<2.5 mm), it is also excellent for contrast imaging deoxygenated hemoglobin and veins due to large difference in absorption for oxy and de-oxy-hemoglobin. The images obtained from 660 nm and 910 nm provide measurements for the blood oxygen saturation level ($SO_2$). Thus a combination of selected wavelengths from spectral measurements of specific chromophores can provide useful information about melanin, oxy-and deoxy-hemoglobin.

For measurements related to melanin, vascular absorption due to de-oxy-hemoglobin, and blood oxygen saturation level, 560 nm, 580 nm, 610 nm, 660 nm, 760 nm, 800 nm and 910 nm wavelengths are selected for imaging through a multispectral nevoscope apparatus 200. The images obtained from 660 nm, 760 nm, 800 and 910 nm can be used to estimate the blood oxygen saturation level ($SO_2$) of the skin-lesion. These measurements can be used in 3-D reconstruction of Hb and $HbO_2$ distributions using a Monte-Carlo simulation based reconstruction method as described herein. Other wavelengths (560 nm, 580 nm, and 610 nm) can be used for visual and 2D analysis of melanin and superficial-to-deep deoxy-hemoglobin-based vascular absorption.

Near-Infrared Imaging for Oxygen Saturation Level Measurement ($HbO_2$ and Hb Absorption)

In the absorption spectra of $HbO_2$ and Hb, as the oxygen saturation goes up, more of the light longer than 800 nm gets absorbed while the shorter wavelength light absorption decreases. To compare the localized absorption difference, we need to obtain the light spectrum with a specific optical path length, and accurately measure how much spectral distortion is caused by the blood absorption, for long and short wavelength range respectfully. In order to analyze the wavelength dependent absorption coefficients, the image obtained from the CCD camera for a fixed wavelength will be analyzed to estimate the absorption coefficients at various wavelength.

Generally the light signal level, $r_s$ decays with increasing depth. The attenuation coefficient is the summation of scattering coefficient $\alpha_s$ and absorption coefficient $\alpha_\alpha(k)$. To simplify this problem, we assume $\alpha_s$ is constant over the bandwidth of the light used. The cumulative spectral distortion at depth l is determined by the light absorption from the end of probe to l, which can be written as:

$$\hat{r}_s(k, l) = r_{s0}\exp\left\{-\int_0^l [\alpha_s(l') + \alpha_a(k, l')]dl'\right\}$$

By averaging $\hat{r}_s(k,l)$ in long and short wavelength range, the following are obtained:

$$\hat{r}_{s\_short}(l) = r_{s0}\exp\left(-2\int_0^l \alpha_s(l')dl'\right)\left\{\exp\left[-\int_0^l \alpha_a(k, l')dl'\right]\right\}_{short}$$

$$= r_{s0}\exp\left(-\int_0^l \alpha_s(l')dl'\right)A_{short}(l)$$

$$\hat{r}_{s\_long}(l) = r_{s0}\exp\left(-2\int_0^l \alpha_s(l')dl'\right)\left\{\exp\left[-\int_0^l \alpha_a(k, l')dl'\right]\right\}_{long}$$

$$= r_{s0}\exp\left(-\int_0^l \alpha_s(l')dl'\right)A_{long}(l)$$

$\{\}_{short,long}$ indicates that the average value of the quantity in side of the brackets in short (e.g. 660 nm) or long wavelength range (e.g. 910 nm).

Although the spatial dependence of absorption coefficient is not exactly known, $A_{short}$ and $A_{short}$ are related to the oxygen saturation level, because the blood absorption coefficient $\alpha_\alpha(k,l)$ is a function of $SO_2$ $$\alpha_a(k,l)=[SO_2(l)]\alpha_{HbO_2}(k)+[1-SO_2(l)]\alpha_{Hb}(k)$$

where $\alpha_{HbO2}$ is the wavelength dependent absorption coefficient of $HbO_2$ corresponding to wavevector k; $\alpha_{Hb}$ is the absorption coefficient of Hb. And $SO_2$ varies as l. R(l) defined as difference of absorption between long and short wavelength light can be computed as $$R(l) = \frac{\hat{r}_{s\_short}(l) - \hat{r}_{s\_long}(l)}{\hat{r}_{s\_short}(l) + \hat{r}_{s\_long}(l)} = \frac{A_{short}(l) - A_{long}(l)}{A_{long}(l) + A_{short}(l)}$$

$R(l)$ is not determined by the absolute amplitude of $\hat{r}_s(k,l)$, but determined by the difference in absorption of the long and the short wavelength range. Therefore, $R(l)$ does not show how much spectral absorption is caused by blood, but rather shows the $SO_2$ related difference in spectral absorption. By images obtained from the short and long wavelength, processing data with aforementioned algorithm, we can obtain 2D $SO_2$ image with $R(l_x, l_z)$.

Computer Classification of Multispectral Nevoscope Images

Figure 12:
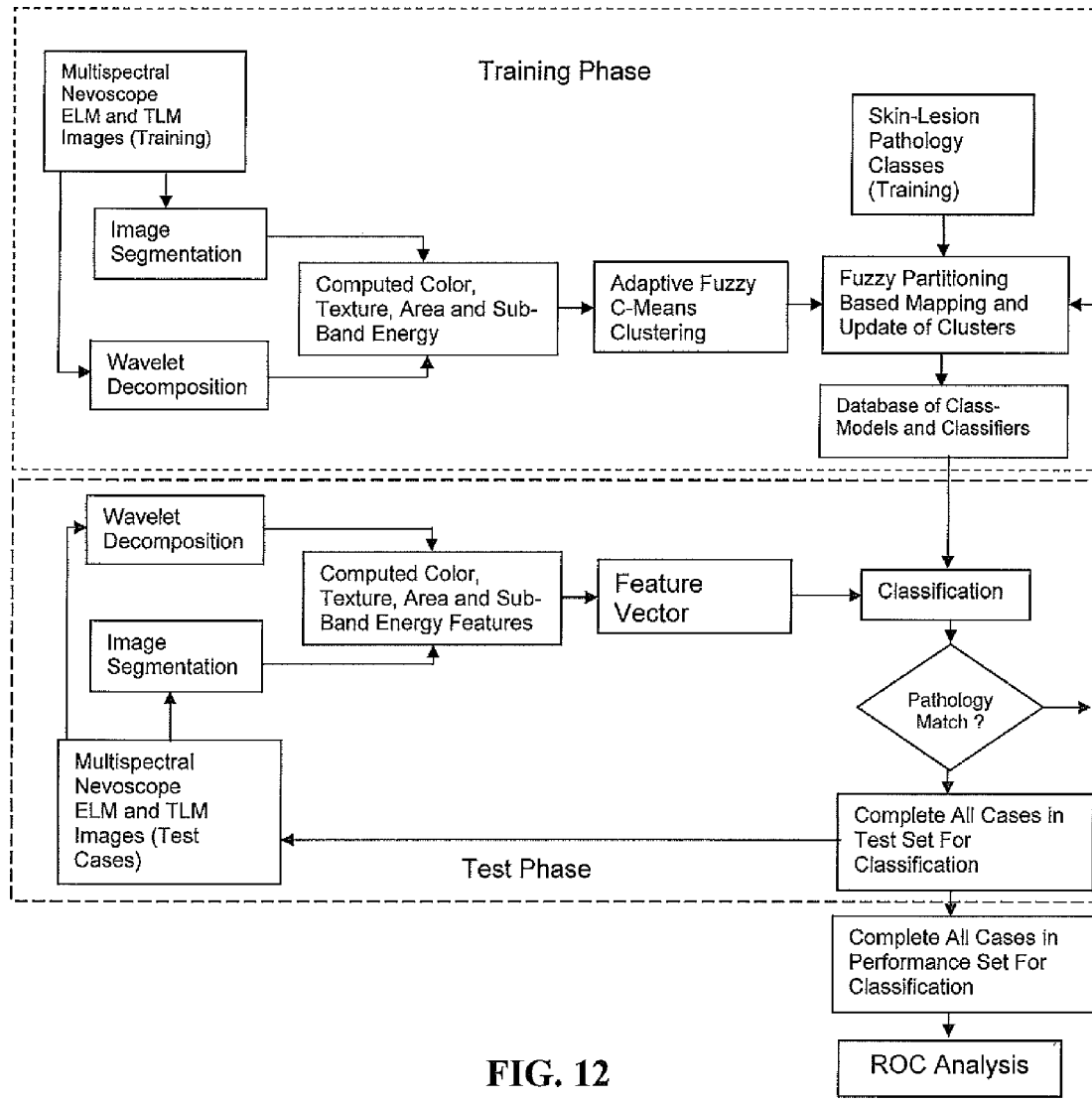
FIG. 12 is a schematic diagram of a computer classification system using adaptive fuzzy clustering and portioning in accordance with at least one embodiment of the present invention.

The disclosed classification system uses an adaptive fuzzy c-means clustering (AFCM) algorithm to provide an optimal set of classifiable clusters of the correlated features extracted from the white-light and multispectral nevoscope images. Now referring to FIG. 12 a schematic diagram of a computer classification system using adaptive Fuzzy clustering and portioning is detailed.

Adaptive Fuzzy c-means Clustering Method

The fuzzy c-means clustering method utilizes an adaptable membership value that can be updated based using the distribution statistics of the data points assigned to the cluster minimizing the following objective function $J_m(U, v)$ $$J_m(U, v) = \sum_{i=1}^{c} \sum_{j=1}^{n} u_{ij}^m d_{ij}^2 = \sum_{i=1}^{c} \sum_{j=1}^{n} u_{ij}^m \|x_j - v_i\|^2$$

where c is the number of clusters, n the number of data feature vectors, $u_{ij}$ is the fuzzy membership, m is the fuzziness index, $x_j$; $j=1 \ldots$, n is the input data feature vectors, $v_i$; $i=1, \ldots$ c are the cluster centroids; and $d_{ij}$ is the Euclidean distance vector. Based on the constraints defined on the distribution statistics of the data points in the clusters, fuzziness index can be defined between 1 and a very large value (maximum allowable variance within a cluster). The membership values can be defined as:

$0 \le u_{ij} \le 1$ for all i,j $$\sum_{i=1}^{c} u_{ij} = 1 \text{ for all } j \text{ and } 0 < \sum_{j=1}^{n} u_{ij} < n \text{ for all } i$$

An adaptive version of the FCM algorithm using a weighted derivative information is described by Pham and Prince, D. L. Pham, J. L. Prince, "Adaptive fuzzy segmentation of magnetic resonance images," IEEE Trans on Med. Imaging, 18, 9, 737-752, (1999). The adaptive FCM algorithm provides a good regularization in the clustering process through the first-and second-order derivative terms that force the bias field to be smooth. As the objective function is minimized for clustering, the minimization of the derivative information provides smooth homogenous clusters.

The objective function $J_{AFCM}(U, v)$ to be minimized for an adaptive fuzzy c-means clustering algorithm can be given as $$J_{ACFM}(U, v) = \sum_{i=1}^{c} \sum_{j=1}^{n} u_{ij}^m \|x_j - g_j v_i\|^2 +$$

-continued $$\lambda_1 \sum_{j=1}^{n} \sum_{r=1}^{R} (D_r \otimes g)_j^2 + \lambda_2 \sum_{j=1}^{n} \sum_{r=1}^{R} \sum_{s=1}^{R} (D_r \otimes D_s \otimes g)_j^2$$

where $g_j$ is the unknown gain field to be estimated during the iterative clustering process, m is the fuzzification index (m>1), R is the dimension of the image, $D_r$ is the derivative operator along the $r^{th}$ dimension of the image, and $\lambda_1$ and $\lambda_2$ are, respectively, the weights for the first-order and second-order derivative terms. Second and third terms in the objective function provide the smoothness constraints.

Figure 13A:
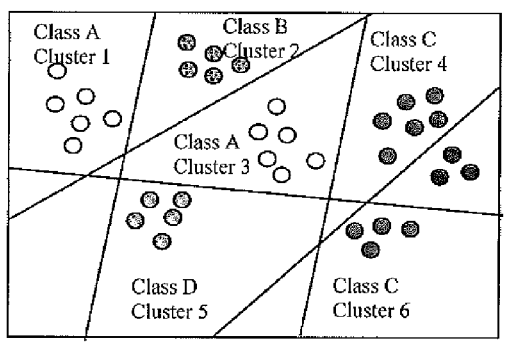
FIG. 13A is a schematic diagram of partitioning of the feature space with hyperplanes in accordance with at least one embodiment of the present invention.

It should be noted that though there may be as many as 14 classes for the lesion classification, the number of clusters c may be much larger than 14 depending on the distribution of data in the feature space. All clusters are required to be homogenous with respect to each category and must satisfy the maximum allowable variance criterion. If a cluster violates the criterion when mapped with the pathology classification labels, it is split and a new value of c is computed. After the mapping and labeling of each cluster is completed, the class models are developed based on the set of clusters and their parameters including mean, variance and fuzzy membership functions. For example, a two-dimensional feature space is shown in FIG. 13A for simplicity to illustrate a hypothetical class distribution. Class A includes two clusters, 1 and 3, while the Class C includes clusters 4 and 6. The model for respective classes must include all clusters and their parameters. These models are stored in the database for each class and updated on a need basis whenever there is disagreement between the pathology and the computed classification from any case in the test set. Thus, the model adapts to the new knowledge and learns new model parameters re-organizing the clusters. The new learning is achieved through the competitive learning approach using a leader-follower clustering algorithm, see, e.g., A. K. Jain and R. C. Dubes, Algorithms for Clustering Data, Prentice Hall, Englewood Cliffs, N.J., (1998). The nearest clusters are polled for the fuzzy membership functions. Based on the "Winner-Take-All" strategy, the cluster with maximum fuzzy membership function is chosen for the inclusion of the new data vector as long as it meets the cluster homogeneity and variance criteria.

Figure 13B:
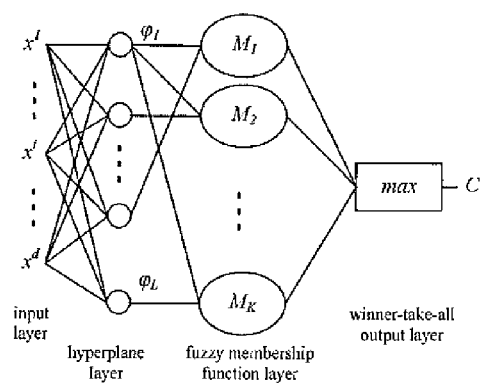
FIG. 13B is a schematic diagram of a winner-takes-all strategy using fuzzy partitions in accordance with at least one embodiment of the present invention.

After the models for pathology classification classes are constructed through labeling of corresponding clusters and their parameters, an integrated competitive learning approach for the classification is developed. In one example hyperplanes as shown can be placed by straight lines in FIG. 13A. Hyperplanes can be placed in the feature space through checking the clusters in each model and creating convex sets around them. W. Grohman and A. P. Dhawan, "Fuzzy convex set based pattern classification of mammographic microcalcifications", Pattern Recognition, vol. 34(7), pp. 119-132 (2001). The creation of convex sets is time consuming but if the cluster parameters are stored for each model class, their respective fuzzy membership functions can be used to partition the feature space efficiently. After the convex sets around the clusters are identified, hyperplanes can be placed for computing the fuzzy classification membership functions to allow final classification using a "Winner-Take-All" strategy as shown in FIG. 13B.

Classification

A fuzzy classification membership function $M_f$ would be constructed to reflect the true shape of the convex subset with the greatest precision possible. The function $M_f$ is defined for each subset $f$ ($f=1, 2, \ldots, K$) of the class model as follows:

$$M_f(x) = \sqrt[L_f]{\prod_{i=1}^{L_f} \theta_i}, \theta_i = \frac{1}{\left(1 + e^{\lambda_{if} \varphi_i x}\right)}$$

where: $L_f$ is the number of separating hyperplanes for the subset $f$, $\phi_i$ is the i-th separating hyperplane function for the subset, in the vector form, x is the input vector in the augmented form, and $\lambda_{if}$ is the steepness (scaling) coefficient for the i-th hyperplane in the subset $f$. The value of $\lambda_{if}$ depends on the depth of convex subset $f$, as projected onto the separating hyperplane $H_i$ (defined by $\phi_i$):

$$\lambda_{if} = \frac{-\log\left(\frac{1-\chi}{\chi}\right)}{\mu_{if}}, \mu_{if} = \frac{1}{n}\sum_{j=1}^{n} \varphi_i x_j$$

where: n is the number of training points in the covex subset $f$, $\phi_i$ is the i-th hyperplane equation in the vector form, $\mu_{if}$ is the depth of the convex subset $f$, as projected onto i-th hyperplane, $x_j$ is an augmented coordinate vector of the j-th point in the subset, and $\chi$ is the center value of the membership function.

The output CO of the classifier is the category C of the convex set fuzzy classification membership function $M_i$ that attains the highest value for the specified input pattern x, i.e.:

$$\left(CO = C \;\middle|\; 1 \le \mathop{\forall f}_{f \ne i} \le K M_f(x) < M_i(x), M_i \in C\right)$$

where: CO is the output of the classifier, K is the number of convex sets obtained during training (number of fuzzy function neurons in the fuzzy membership function layer), $M_i$ is the highest fuzzy classification membership function value for the input x, and C is the model class of convex subset used to construct membership function $M_i$.

Applicants have attempted to disclose all embodiments and applications of the described subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All references cited herein are incorporated fully by reference.

What is claimed is:

1. A method of reconstructing skin lesion images comprising transilluminating a skin lesion using a nevoscope by applying visible light and near-infrared wavelengths in the range of 400 nm to 1000 nm in a converging ring to the skin lesion, dividing a detector space of the nevoscope into a plurality of concentric rings with equal width, wherein an innermost ring contains a plurality of detectors with equal size and remaining rings are split into a number of detectors which maintain the same area as the detectors in the innermost ring, collecting information about absorption and scattering properties of melanin, oxyhemoglobin and/or deoxyhemoglobin of skin layers and the skin lesion, the collecting step comprising obtaining reflectance-based absorption measurements with different levels of depth of penetration to estimate volumes of melanin, oxyhemoglobin and deoxyhemoglobin, retrieving information regarding the distribution of melanin, oxyhemoglobin and/or deoxyhemoglobin in the skin layers and lesion, applying a shape-based multi-constrained algorithm to the collected and retrieved information, and using results obtained from applying the algorithm to reconstruct a skin lesion image based on shapes of the melanin, oxyhemoglobin and/or deoxyhemoglobin wherein the melanin, oxyhemoglobin and/or deoxyhemoglobin are delineated by a first and a second cubic tensor-product B-spline surface, wherein the multi-constrained algorithm comprises a linearized forward model evaluated by Monte Carlo simulation in terms of typical optical properties of normal skin, generating a Jacobian matrix, applying a genetic algorithm to generate predicted shape, performing a sampling function, evaluating the Jacobian matrix by recording trajectories for one detector of a given ring and generating trajectories of remaining detectors by rotating recorded trajectories, and applying the Jacobian matrix to the result of the sampling function to generate a best possible reconstruction solution.

2. The method according to claim 1 wherein malignant melanoma is represented by shape parameters of a melanin part and one or more of an oxyhemoglobin or deoxyhemoglobin part and these parameters are grouped into genetic algorithms.

3. The method according to claim 1 wherein the wavelengths are in the range of 500 nm to 960 nm.

4. The method according to claim 1 wherein the first cubic tensor-product B-spline surface is represented as function $f_1(x,y)$ which corresponds to a depth of the skin lesion from an epidermal layer at a position (x,y), positioning an N×N rectangular grid to lie over the epidermal layer, sampling the function $f_1(x,y)$ to N×N discrete values $f_{d1}(X,Y)$ wherein (x,y) is continuous and (X,Y) is N×N numbers of discrete sampling positions, interpolating the discrete values by the cubic tensor-product B-spline which satisfies the condition $$f_{d1}(X, Y) = \sum_{i=1}^{N} \sum_{j=1}^{N} c_1(i, j)\beta^3(X - i, Y - j)$$

and approximating the original function $f_1(x,y)$ by $$f_{B1}(x, y) = \sum_{i=1}^{N} \sum_{j=1}^{N} c_1(i, j)\beta^3(x - i, y - j)$$

wherein $\beta^3(x-i, y-j) = \beta^3(x-i)g\beta^3(y-j)$ is the tensor product of one-dimensional cubic B-spline basis $\beta^3(x-i)$ and $\beta^3(y-j)$, and $c_1(i,j)$ is B-spline coefficient.

5. The method according to claim 4 wherein the parameters to determine the melanin shape are N×N discrete values $f_{d1}(X,Y)$.

6. The method according to claim 4 wherein the parameters to determine the melanin shape are the corresponding B-spline coefficients $c_1(i,j)$.

7. The method according to claim 4 wherein the second cubic tensor-product B-spline surface is defined by N×N discrete values $f_{d2}(X,Y)$.

8. The method according to claim 4 wherein the second cubic tensor-product B-spline surface is defined by $z_d(X,Y) = f_{d2}(X,Y) - ff_{d1}(X,Y)$ which is the thickness of blood region between the first surface and the second surface.

9. A method of reconstructing skin lesion images comprising transilluminating a skin lesion using a nevoscope by applying visible light and near-infrared wavelengths in the range of 400 nm to 1000 nm in a converging ring to the skin lesion, collecting information about absorption and scattering properties of melanin, oxyhemoglobin and/or deoxyhemoglobin of skin layers and the skin lesion, the collecting step comprising obtaining reflectance-based absorption measurements with different levels of depth of penetration to estimate volumes of melanin, oxyhemoglobin and deoxyhemoglobin, retrieving information regarding the distribution of melanin, oxyhemoglobin and/or deoxyhemoglobin in the skin layers and lesion, applying a shape-based multi-constrained algorithm to the collected and retrieved information, and using results obtained from applying the algorithm to reconstruct a skin lesion image based on shapes of the melanin, oxyhemoglobin and/or deoxyhemoglobin wherein the melanin, oxyhemoglobin and/or deoxyhemoglobin are delineated by a first and a second cubic tensor-product B-spline surface, and wherein the first cubic tensor-product B-spline surface is represented as function $f_1(x,y)$ which corresponds to a depth of the skin lesion from an epidermal layer at a position (x,y), positioning an N×N rectangular grid to lie over the epidermal layer, sampling the function $f_1(x,y)$ to N×N discrete values $f_{d1}(X,Y)$ wherein (x,y) is continuous and (X,Y) is N×N numbers of discrete sampling positions, interpolating the discrete values by the cubic tensor-product B-spline which satisfies the condition $$f_{d1}(X, Y) = \sum_{i=1}^{N} \sum_{j=1}^{N} c_1(i, j)\beta^3(X - i, Y - j)$$

and approximating the original function $f_1(x,y)$ by $$f_{B1}(x, y) = \sum_{i=1}^{N} \sum_{j=1}^{N} c_1(i, j)\beta^3(x - i, y - j)$$

wherein $\beta^3(x-i, y-j) = \beta^3(x-i)g\beta^3(y-j)$ is the tensor product of one-dimensional cubic B-spline basis $\beta^3(x-i)$ and $\beta^3(y-j)$, and $c_1(i,j)$ is B-spline coefficient.

10. The method according to claim 9 wherein the parameters to determine the melanin shape are N×N discrete values $f_{d1}(X,Y)$.

11. The method according to claim 9 wherein the parameters to determine the melanin shape are the corresponding B-spline coefficients $c_1(i,j)$.

12. The method according to claim 9 wherein the second cubic tensor-product B-spline surface is defined by N×N discrete values $f_{d2}(X,Y)$.

13. The method according to claim 9 wherein the second cubic tensor-product B-spline surface is defined by $z_d(X,Y) = f_{d2}(X,Y) - f_{d1}(X,Y)$ which is the thickness of blood region between the first surface and the second surface.

14. The method according to claim 9 wherein the multi-constrained algorithm comprises a linearized forward model evaluated by Monte Carlo simulation in terms of typical optical properties of normal skin, generating a Jacobian matrix, applying a genetic algorithm to generate predicted shape, performing a sampling function, and applying the Jacobian matrix to the result of the sampling function to generate a best possible reconstruction solution.

15. The method according to claim 9 wherein malignant melanoma is represented by shape parameters of a melanin part and one or more of an oxyhemoglobin or deoxyhemoglobin part and these parameters are grouped into genetic algorithms.

16. The method according to claim 9 wherein the wavelengths are in the range of 500 nm to 960 nm.

17. The method according to claim 9 comprising dividing a detector space of the nevoscope into a plurality of concentric rings with equal width, wherein an innermost ring contains a plurality of detectors with equal size and remaining rings are split into a number of detectors which maintain the same area as the detectors in the innermost ring, and evaluating a Jacobian matrix by recording trajectories for one detector of a given ring and generating trajectories of remaining detectors by rotating recorded trajectories.

* * * * *